(12) United States Patent
Silverman et al.

(10) Patent No.: US 7,704,203 B2
(45) Date of Patent: Apr. 27, 2010

(54) KIT FOR TREATING GASTROINTESTINAL TRACT

(75) Inventors: David E. Silverman, Palo Alto, CA (US); Alan Stein, Moss Beach, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 915 days.

(21) Appl. No.: 10/386,046

(22) Filed: Mar. 10, 2003

(65) Prior Publication Data
US 2003/0171645 A1 Sep. 11, 2003

Related U.S. Application Data

(60) Division of application No. 09/851,651, filed on May 8, 2001, now Pat. No. 6,533,717, which is a division of application No. 09/286,245, filed on Apr. 5, 1999, now Pat. No. 6,251,063, which is a continuation-in-part of application No. 09/232,056, filed on Jan. 15, 1999, now Pat. No. 6,238,335.

(60) Provisional application No. 60/111,884, filed on Dec. 11, 1998.

(51) Int. Cl.
*A61F 2/00* (2006.01)
(52) U.S. Cl. ...................................... 600/37
(58) Field of Classification Search ................. 128/897, 128/898, DIG. 25; 600/29–32; 606/1; 623/7, 623/8; 424/502; 206/363–366
See application file for complete search history.

(56) References Cited

U.S. PATENT DOCUMENTS

| | | | |
|---|---|---|---|
| 3,094,122 A | 6/1963 | Gauthier et al. | |
| 3,204,634 A | 9/1965 | Koehn | |
| 4,271,827 A | 6/1981 | Angelchik | |
| 4,351,333 A | 9/1982 | Lazarus et al. | |
| 4,424,208 A | 1/1984 | Wallace et al. | |
| 4,522,302 A * | 6/1985 | Paikoff | 206/570 |
| 4,582,640 A | 4/1986 | Smestad et al. | |
| 4,763,667 A | 8/1988 | Manzo | |
| 4,773,393 A | 9/1988 | Haber et al. | |
| 4,803,075 A | 2/1989 | Wallace et al. | |
| 4,837,285 A | 6/1989 | Berg et al. | |

(Continued)

FOREIGN PATENT DOCUMENTS

AU    A-34223/95    5/1996

(Continued)

OTHER PUBLICATIONS

Webster's Ninth New Collegiate Dictionary, 1991; "solution", p. 1123, 2 total pages.*

(Continued)

*Primary Examiner*—Samuel G Gilbert
(74) *Attorney, Agent, or Firm*—Mayer & Williams P.C.; David B. Bonham; Keum J. Park

(57) ABSTRACT

A method for treating a gastrointestinal tract in a body of a mammal. At least one nonaqueous solution is introduced into the wall. A nonbiodegradable solid is formed in the wall from the at least one nonaqueous solution to treat the wall. A kit for use in the procedure is provided.

11 Claims, 8 Drawing Sheets

U.S. PATENT DOCUMENTS

| | | | |
|---|---|---|---|
| 4,932,942 A | 6/1990 | Maslanka | |
| 5,007,940 A | 4/1991 | Berg | |
| 5,067,965 A | 11/1991 | Ersek et al. | |
| 5,116,387 A | 5/1992 | Berg | |
| 5,158,573 A | 10/1992 | Berg | |
| 5,204,382 A | 4/1993 | Wallace et al. | |
| 5,258,028 A | 11/1993 | Ersek et al. | |
| 5,263,931 A * | 11/1993 | Miller | 604/103.13 |
| 5,301,682 A | 4/1994 | Debbas | |
| 5,314,473 A | 5/1994 | Godin | |
| 5,322,510 A | 6/1994 | Lindner et al. | |
| 5,336,263 A | 8/1994 | Ersek et al. | |
| 5,385,561 A | 1/1995 | Cerny | |
| 5,403,311 A * | 4/1995 | Abele et al. | 606/49 |
| 5,451,406 A | 9/1995 | Lawin et al. | |
| 5,480,644 A | 1/1996 | Freed | |
| 5,490,984 A | 2/1996 | Freed | |
| 5,580,568 A | 12/1996 | Greff et al. | |
| 5,584,861 A | 12/1996 | Swain et al. | |
| 5,645,559 A | 7/1997 | Hachtman et al. | |
| 5,667,767 A | 9/1997 | Greff et al. | |
| 5,667,778 A | 9/1997 | Atala | |
| 5,695,480 A | 12/1997 | Evans et al. | |
| 5,702,361 A | 12/1997 | Evans et al. | |
| 5,709,657 A | 1/1998 | Zimmon | |
| 5,755,658 A * | 5/1998 | Wallace et al. | 600/30 |
| 5,755,730 A | 5/1998 | Swain et al. | |
| 5,785,642 A | 7/1998 | Wallace et al. | |
| 5,792,153 A | 8/1998 | Swain et al. | |
| 5,792,478 A * | 8/1998 | Lawin et al. | 424/502 |
| 5,830,178 A | 11/1998 | Jones et al. | |
| 5,855,615 A * | 1/1999 | Bley et al. | 424/423 |
| 5,861,036 A | 1/1999 | Godin | |
| 5,958,444 A | 9/1999 | Wallace et al. | |
| 6,010,515 A | 1/2000 | Swain et al. | |
| 6,059,719 A | 5/2000 | Yamamoto et al. | |
| 6,096,021 A * | 8/2000 | Helm et al. | 604/509 |
| 6,098,629 A | 8/2000 | Johnson et al. | |
| 6,099,567 A | 8/2000 | Badylak et al. | |
| 6,146,418 A | 11/2000 | Berman | |
| 6,234,955 B1 | 5/2001 | Silverman et al. | |
| 6,238,335 B1 | 5/2001 | Silverman et al. | |
| 6,248,058 B1 | 6/2001 | Silverman et al. | |
| 6,251,063 B1 | 6/2001 | Silverman et al. | |
| 6,251,064 B1 | 6/2001 | Silverman et al. | |
| 6,335,028 B1 | 1/2002 | Vogel et al. | |
| 6,338,345 B1 | 1/2002 | Johnson et al. | |
| 6,358,197 B1 | 3/2002 | Silverman et al. | |
| 6,425,854 B1 | 7/2002 | Galt et al. | |
| 6,478,775 B1 | 11/2002 | Galt et al. | |
| 6,530,878 B2 | 3/2003 | Silverman et al. | |
| 6,533,717 B2 | 3/2003 | Silverman et al. | |
| 6,540,789 B1 | 4/2003 | Silverman et al. | |
| 6,555,104 B2 | 4/2003 | Wallace et al. | |
| 6,569,417 B2 | 5/2003 | Wallace et al. | |
| 6,575,896 B2 | 6/2003 | Silverman et al. | |
| 6,576,019 B1 | 6/2003 | Atala | |
| 6,591,838 B2 | 7/2003 | Durgin | |
| 6,595,909 B2 | 7/2003 | Silverman et al. | |
| 6,595,910 B2 | 7/2003 | Silverman et al. | |
| 6,695,764 B2 | 2/2004 | Silverman et al. | |
| 6,802,868 B2 | 10/2004 | Silverman et al. | |
| 7,044,979 B2 | 5/2006 | Silverman et al. | |
| 7,056,277 B2 | 6/2006 | Silverman et al. | |
| 7,249,601 B2 | 7/2007 | Silverman et al. | |
| 2003/0171645 A1 | 9/2003 | Silverman et al. | |
| 2003/0199731 A1 | 10/2003 | Silverman et al. | |
| 2004/0010182 A1 | 1/2004 | Silverman et al. | |
| 2004/0249239 A1 | 12/2004 | Silverman et al. | |
| 2006/0235261 A1 | 10/2006 | Silverman et al. | |
| 2006/0249165 A1 | 11/2006 | Silverman et al. | |

FOREIGN PATENT DOCUMENTS

| | | |
|---|---|---|
| JP | 4-504974 | 9/1992 |
| JP | 6-26284 | 7/1994 |
| JP | 9-24095 | 1/1997 |
| WO | WO 97/04657 | 2/1997 |
| WO | WO 97/19643 | 6/1997 |
| WO | WO 97/45131 | 12/1997 |
| WO | WO 98/01088 | 1/1998 |
| WO | WO 98/17200 | 4/1998 |
| WO | WO 98/17201 | 4/1998 |

OTHER PUBLICATIONS

Society of Am. Gastrointestinal Endoscopic Surgeons, Los Angeles, CA, "Granting of Privileges for Laparascopic General Surgery", (Mar. 1991), *Am. Jrnl. of Surgery*, vol. 161, pp. 324-325.

Aye, R.W. et al., "Early Results With the Laparoscopic Hill Repair", (May 1994), *Am. Jrnl. of Surgery*, vol. 167, pp. 542-546.

Collard, J.M. et al., "Laparoscopic Antireflux Surgery/What is Real Progress?", (1994), *Annals of Surgery*, vol. 220, No. 2, pp. 146-154.

DeMeester, T.R. et al., "Nissen Fundoplication for Gastroesophageal Reflux Disease", (1986), *Annals of Surgery*, vol. 204, No. 1, pp. 9-20.

Donahue, P.E. et al., "The Floppy Nissen Fundoplication/Effective Long-term Control of Pathologic Reflux", (Jun. 1985), *Arch Surg*, vol. 120, pp. 663-668.

P. Donahue et al., "Endoscopic Sclerosis Of The Gastric Cardia For Prevention Of Experimental Gastroesophageal Reflux", (1990) *Gastrointestinal Endoscopy*, pp. 253-258.

Ellis, Jr., F.H., "The Nissen Fundoplication", (1992), *Ann. Thorac. Surg.*, vol. 54, pp. 1231-1235.

Grande, L. et al., "Value of Nissen fundoplication in patients with gastro-oesophageal reflux judged by long-term sympton control", (1994), *Brit. Jrnl. of Surgery*, vol. 81, pp. 548-550.

Hill, L.D. et al., "Laparoscopic Hill Repair", (Jan. 1994), *Contemporary Surgery*, vol. 44, No. 1, pp. 13-20.

Hunter, J.G. et al., "A Physiologic Approach to Laparoscopic Fundoplication for Gastroesophageal Reflux Disease", (1996), *Annals of Surgery*, vol. 223, No. 6, pp. 673-687.

Ireland, A.C. et al., "Mechanisms underlying the antireflux action of fundoplication", (1993), *Gut*, vol. 34, pp. 303-308.

Johansson, J. et al., "Outcome 5 years after 360° fundoplication for gastro-oesophageal reflux disease", (Jan. 1993), *Brit. Jnl. of Surgery*, vol. 80, pp. 46-49.

Kauer, W.K.H. et al., "Mixed Reflux of Gastric and Duodenal Juices Is More Harmful to the Esophagus than Gastric Juice Alone/The Need for Surgical Therapy Re-Emphasized", (1995) *Annals of Surgery*, vol. 222, No. 4, pp. 525-533.

Klingman, R.R. et al., "The Current Management of Gastroesophageal Reflux", (1991), *Adv. Surg.*, vol. 24, pp. 259-291.

Little, A.G., "Mechanisms of Action of Antireflux Surgery: Theory and Fact", (1992), *World Jnl. of Surgery*, vol. 16, pp. 320-325.

Luostarinen, M., "Nissen Fundoplication for Reflux Esophagitis/Long-Term Clinical and Endoscopic Results in 109 of 127 Consecutive Patients", (1993), *Annals of Surgery*, vol. 217, No. 4, pp. 329-337.

Luostarinen, M. et al., "Fate of Nissen fundoplication after 20 years. A clinical, endoscopical, and functional analysis", (1993), *Gut*, vol. 34, pp. 1015-1020.

Malizia, A. et al., "Migration and Granulomatous Reaction After Periurethral injection of Polytef (Teflon)", (Jun. 1984), *JAMA*, vol. 251, No. 24, pp. 3277-3281.

Martin, C. et al., "Collis-Nissen Gastroplasty Fundoplication For Complicated Gastro-Oesophageal Reflux Disease", (1992), *Aust. N.Z. Jnl. Surg.*, vol. 62, pp. 126-129.

O'Connor, K.W. et al., "Endoscopic placement of collagen at the lower esophageal sphincter to inhibit gastroesophageal reflux: a pilot study of 10 medically intractable patients", (1988), *Gastrointestinal Endoscopy*, vol. 34, No. 2, pp. 106-112.

O'Connor, K. W. et al., "An experimental endoscopic technique for reversing gastroesophageal reflux in dogs by injecting inert material in the distal esophagus", (1984) Gatrointestinal Endoscopy, vol. 30, No. 5, pp. 275-280.

Ortiz, A. et al., "Conservative treatment versus antireflux surgery in Barrett's oesophagus: long-term results of a prospective study", (1996), *Brit. Jnl. of Surg.*, vol. 83, 274-278.

Politano, V. et al., "Periurethral Teflon Injection for Urinary Incontinence", (Feb. 1974) *Jnl.Urology*, vol. 111, pp. 180-183.

Pope, C., "The Quality of Life Following Antireflux Surgery", (1992), *World Jnl. of Surgery*, vol. 16, pp. 355-358.

Schulman, C.C. et al., "Endoscopic injections of Teflon to treat urinary incontinence in women", (Jan. 21, 1984) *BMJ*, vol. 228, p. 192.

Shafik, A., "Intraesophageal Polytef injection for the treatment of reflux esophagitis", (1996), *Surgical Endoscopy*, pp. 329-331.

Shirazi, S.S. et al., "Long-term Follow-up for Treatment of Complicated Chronic Reflux Esophagitis", (May 1987), *Arch Surg*, vol. 122, 548-552.

Spechler, S.J. et al., "Comparison of Medical and Surgicl Therapy for Complicated Gastroesophageal Reflux Disease in Veterans", (Mar. 19, 1992), *NE Jnl. of Med*, vol. 326, No. 12, pp. 786-792.

Spechler, S.J. et al., "The Columnar-Lined Esophagus, Intestinal Metaplasia, and Norman Barrett", (1996), *Gastroenterology*, vol. 110, pp. 614-621.

Thor, K.B. et al., "A Long-Term Randomized Prospective Trial of the Nissen Procedure Versus a Modified Toupet Technique", (Dec. 1989), *Ann. Surg.*, vol. 210, No. 6, pp. 719-724.

Vaezi, M.F. et al., "Synergism of acid and duodenogastroesophageal reflux in complicated Barrett's esophagus", (1995), *Surgery*, vol. 117, pp. 699-704.

Walker, R.D. et al., "Injectable Bioglass as a Potential Substitute for Injectable Polytetrafluoroethylene", (Aug. 1992), *J. Urol.*, vol. 148, pp. 645-647.

Waring, J.P. et al., "The Preoperative Evaluation of Patients Considered for Laparoscopic Antireflux Surgery", (1995), *Am. Jnl. of Gastroenterology*, vol. 90, No. 1, pp. 35-38.

New Riverside University Dictionary, 1984; The Riverside Publishing Company, pp. 774-775, 778 & 1154.

\* cited by examiner

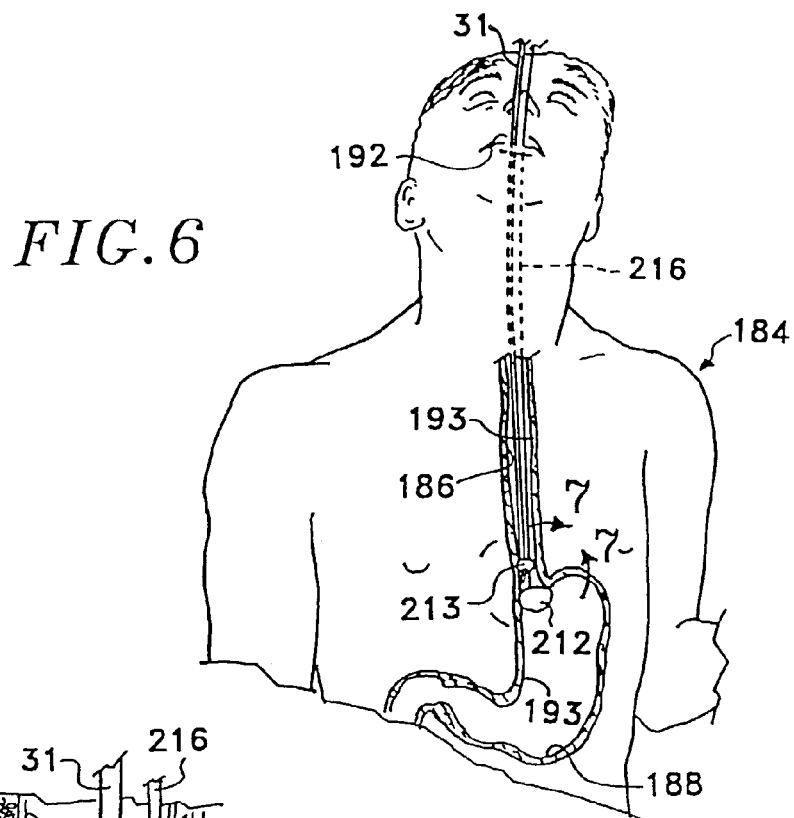
FIG. 6
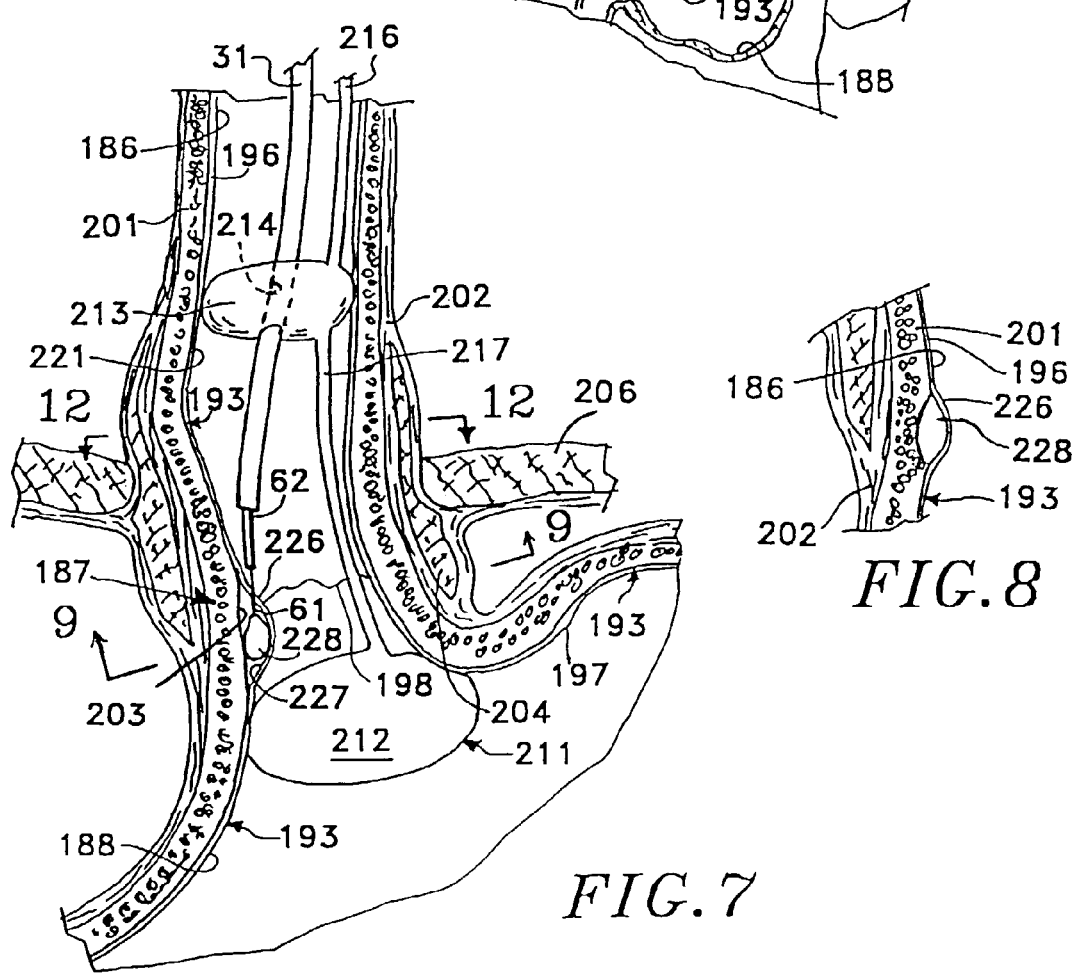
FIG. 7
FIG. 8

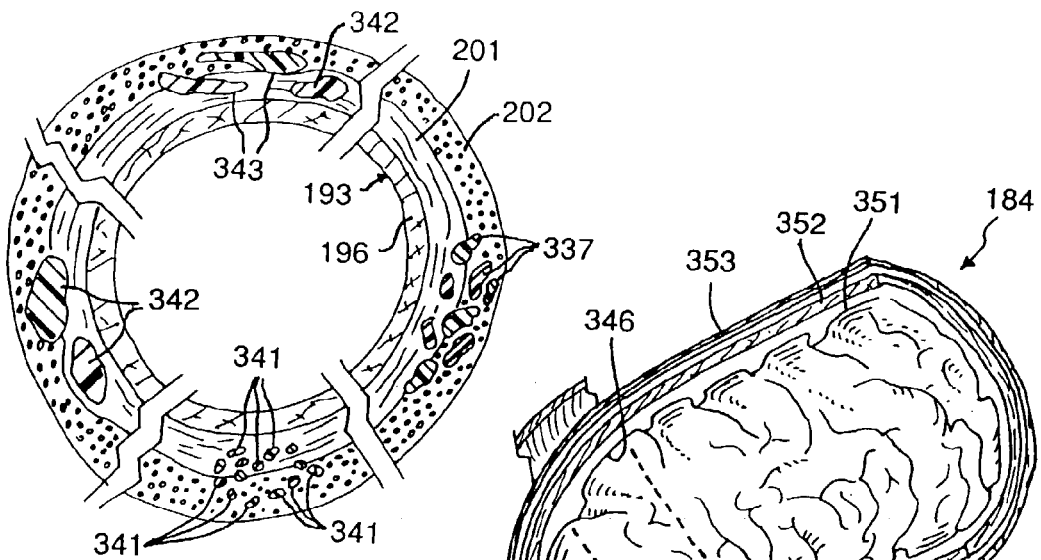
FIG. 20
FIG. 21
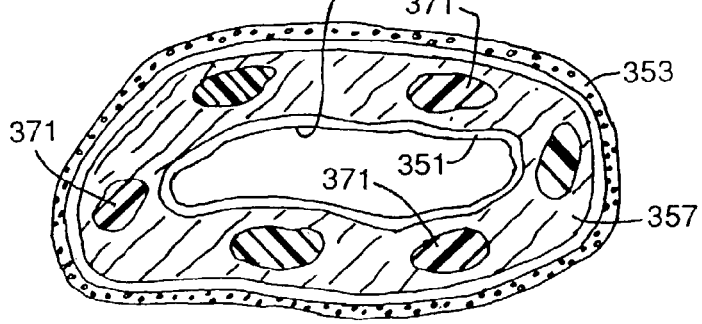
FIG. 22
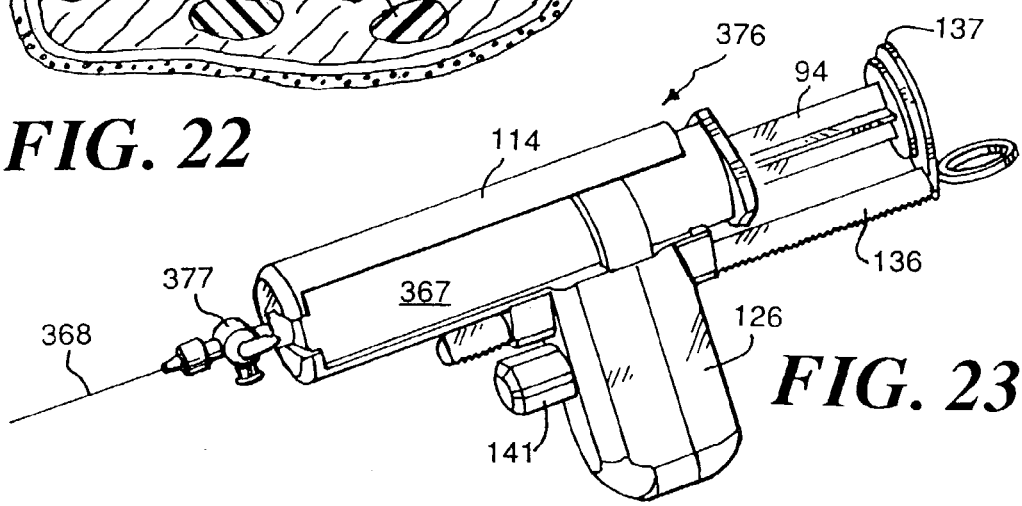
FIG. 23

KIT FOR TREATING GASTROINTESTINAL TRACT

This application is a division of U.S. utility patent application Ser. No. 09/851,651 filed May 8, 2001 now U.S. Pat. No. 6,533,717, which is a division of U.S. patent application Ser. No. 09/286,245 filed Apr. 5, 1999, now U.S. Pat. No. 6,251,063, which is a continuation-in-part of U.S. patent application Ser. No. 09/232,056 filed Jan. 15, 1999, now U.S. Pat. No. 6,238,335, and claims priority to U.S. provisional patent application Ser. No. 60/111,884 filed Dec. 11, 1998, the entire contents of each of which are incorporated herein by this reference.

This invention pertains to the treatment of the gastrointestinal tract and, more particularly, to the formation of implants in the wall forming the gastrointestinal tract.

Gastroesophageal reflux disease (GERD) is a failure of the anti-reflux barrier, allowing abnormal reflux of gastric contents into the esophagus of the gastrointestinal tract. Gastroesophageal reflux disease is a disorder which is usually characterized by a defective lower esophageal sphincter (LES), a gastric emptying disorder with or without failed esophageal peristalsis. The disease usually manifests itself during "transient lower esophageal sphincter relaxation" episodes, the frequency of which is greatly increased in patients who reflux. Medical or drug therapy is the first line of management for gastroesophageal refluxes. However, drug management does not address the condition's mechanical etiology. Thus symptoms recur in a significant number of sufferers within one year of drug withdrawal. In addition, while medical therapy may effectively treat the acid-induced symptoms of gastroesophageal reflux disease, esophageal mucosal injury may continue due to ongoing alkaline reflux. Since gastroesophageal reflux disease is a chronic condition, medical therapy involving acid suppression and/or promotility agents may be required for the rest of a patient's life.

The expense and psychological burden of a lifetime of medication dependence, undesirable life style changes, uncertainty as to the long term effects of some newer medications and the potential for persistent mucosal changes despite symptomatic control, all make surgical treatment of gastroesophageal reflux disease an attractive option. Unfortunately, surgical intervention is a major operation with all attendant morbidities, mortality and risk of failure requiring further surgery in the case of over-correction. Laparoscopic surgery requires a very high level of skill and special training for it to be successful.

Minimally invasive approaches have been tried for treating gastroesophageal reflux disease, but have had only transient effects. Such approaches include the injection of sclerosing agents at the level of the gastric cardia. Injections of other biodegradable substances have been tried, but have proven to provide only a short duration of activity.

Fecal incontinence, which is most common in the elderly, is the loss of voluntary control to retain stool in the rectum. In most patients, fecal incontinence is initially treated with conservative measures, such as biofeedback training or alteration of the stool consistency. Biofeedback is successful in approximately two-thirds of patients who retain some degree of rectal sensation and functioning of the external anal sphincter. However, multiple sessions are often necessary, and patients need to be highly motivated. Electronic home biofeedback systems are available and may be helpful as adjuvant therapy. Several surgical approaches to fecal incontinence have been tried, with varying success, when conservative management has failed. These treatments include sphincter repair, gracilis or gluteus muscle transposition to reconstruct an artificial sphincter and colostomy. The approach that is used depends on the cause of the incontinence and the expertise of the surgeon. For example, biodegradable compounds have been injected or introduced into the anal sphincter to bulk or augment the rectal wall. Unfortunately, such biodegradable compounds are resorbed by the body and thus become ineffective over time. In addition, such surgical interventions suffer from the same disadvantages discussed above with respect to GERD.

In general, it is an object of the present invention to provide a minimally invasive method and apparatus for treating the gastrointestinal tract.

Another object of the invention is to provide a method and apparatus of the above character for injecting a material into the wall forming the gastrointestinal tract to form one or more implants in the wall for augmenting or bulking the wall.

Another object of the invention is to provide a method and apparatus of the above character in which the material is a nonbiodegradable material.

Another object of the invention is to provide a method and apparatus of the above character in which the material is injected as at least one solution and thereafter forms a solid.

Another object of the invention is to provide a method and apparatus of the above character in which the at least one solution includes a solution from which a nonbiodegradable solid precipitates.

Another object of the invention is to provide a method and apparatus of the above character in which the solution includes a biocompatible polymer and a biocompatible solvent.

Another object of the invention is to provide a method and apparatus of the above character in which an aqueous or physiologic solution is introduced into the wall to condition the wall.

Another object of the present invention is to provide a method and apparatus of the above character for treating gastroesophageal reflux disease in which one or more implants are formed in the wall forming the esophagus and/or stomach in the vicinity of the lower esophageal sphincter.

Another object of the invention is to provide a method of the above character for treating fecal incontinence in which one or more implants are formed in the wall in the vicinity of the anal sphincter.

Another object of the invention is to provide a method of the above character in which one or more implants of a nonbiodegradable material are formed in the anal sphincter for augmenting the anal sphincter.

Another object of the invention is to provide a method and apparatus of the above character which is reversible.

Additional objects and features of the invention will appear from the following description from which the preferred embodiments are set forth in detail in conjunction with the accompanying drawings.

FIG. 6 is a schematic view of the apparatus for treating gastroesophageal reflux disease of FIG. 1 practicing the method of the present invention.

FIG. 7 is an enlarged elevational view of the lower esophageal sphincter of FIG. 6 taken along the line 7-7 of FIG. 6.

FIG. 8 is an enlarged elevational view, similar to FIG. 7, of a portion of the lower esophageal sphincter showing another step of the method of the present invention.

FIG. 20 is a cross-sectional view, similar to FIG. 19, of the lower esophageal sphincter at the level of the gastric cardia as treated by the method of the present invention.

FIG. 21 is a sectional view of a portion of the human body in which a portion of the anal sphincter is being augmented by a method of the present invention.

FIG. 22 is a cross-sectional of a portion of the anal sphincter of FIG. 21 taken along the line 22-22 of FIG. 21.

FIG. 23 is a perspective view of an apparatus for use in the method for treating the anal sphincter of the present invention.

In general, a method for treating a gastrointestinal tract in a body of a mammal is provided. At least one nonaqueous solution is introduced into the wall. A nonbiodegradable solid is formed in the wall from the at least one nonaqueous solution to treat the wall. A kit for use in the procedure is provided.

Figure 1:
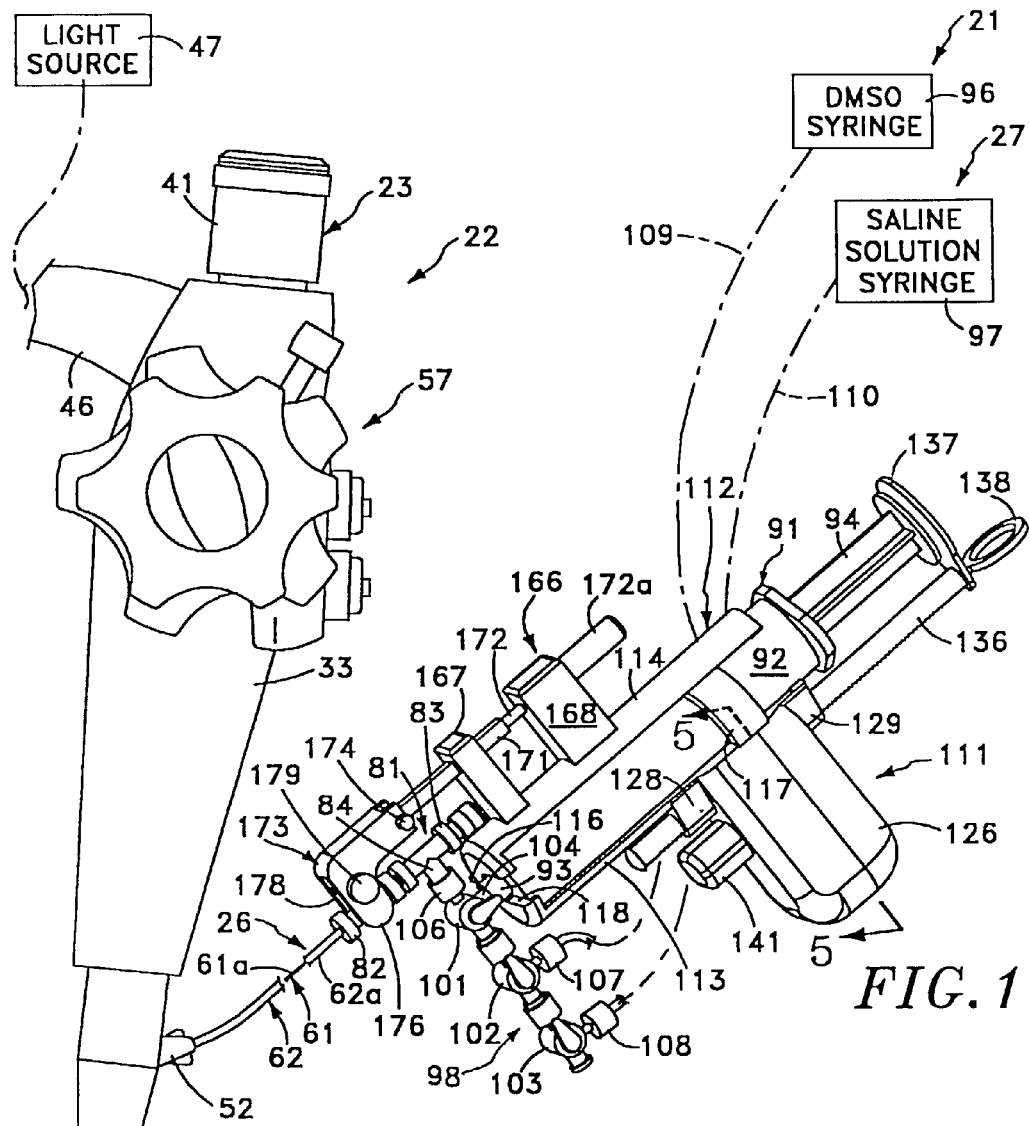
FIG. 1 is a perspective view of an apparatus for treating gastroesophageal reflux disease of the present invention.

The method of the present invention can be performed with an apparatus of the type shown in FIG. 1. Apparatus or medical device 21 shown therein includes a probe member or probe 22 having an optical viewing device 23. A needle assembly 26 is slidably carried by probe 22. Treatment device 21 further includes a supply assembly 27 mounted to the proximal end portion of needle assembly 26.

Figure 2:
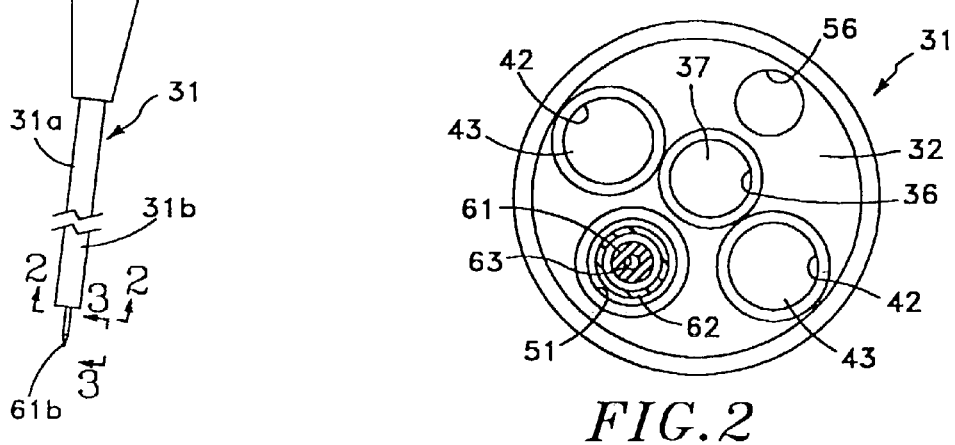
FIG. 2 is a cross-sectional view of a portion of the apparatus of FIG. 1 taken along the line 2-2 of FIG. 1.

A conventional or other suitable gastroscope or endoscope can be used for probe 22. The exemplary probe 22 shown in FIG. 1 is an Olympus CF Type 40L/I endoscope made by Olympus Corporation of Tokyo Japan. Probe 22 includes a flexible elongate tubular member or insertion tube 31 having proximal and distal extremities 31a and 31b and a distal face 32. Insertion tube 31 has been sectioned in FIG. 1 so that only a portion of proximal extremity 31a and distal extremity 31b are shown. A handle means or assembly is coupled to proximal extremity 31a of the insertion tube 31 and includes a conventional handle 33. The tubular insertion tube 31 is provided with a plurality of bores or passageways extending from proximal extremity 31a to distal extremity 31b. A plurality of five such passageways, including a central passageway 36, are shown in FIG. 2.

An optical viewing device 23 is formed integral with conventional probe 22 and has an optical element or objective lens 37 carried by the central passageway 36 of insertion tube 31. The lens 37 has a field of view at distal face 32 which permits the operator to view forwardly of insertion tube distal extremity 31b. Optical viewing device 37 further includes an eye piece 41 mounted on the proximal end of handle 33. Second and third illumination passageways 42 are provided in insertion tube 31 peripherally of central passageway 36 for carrying respective light fiber assemblies or light guides 43. A connection cable 46, a portion of which is shown in FIG. 1, extends from handle 33 to a conventional light source 47. First and send light guides 43 extend through insertion tube 31 and cable 46 for providing illumination forwardly of insertion tube 31.

A working passageway or channel 51 is further provided in insertion tube 31 and extends to a side port 52 formed in handle 33. An additional passageway 56 extends through insertion tube 31 and can be used as an air and/or water outlet. Insertion tube 31 is flexible so as to facilitate its insertion and advancement through a body and is provided with a bendable distal end for selectively directing distal face 32 in a desired direction. A plurality of finger operable controls 57 are provided on handle 33 for, among other things, operating the bendable distal end of insertion tube 31 and the supply and removal of fluids through the insertion tube 31.

Needle assembly 26 can be of any conventional type such as a modified sclerotherapy needle similar to the Bard® Flex-itip™ needle manufactured by C.R. Bard, Inc. of Billerica, Md. Needle assembly 26 includes a needle member or needle 61 having a proximal end portion 61a and a distal end portion 61b and an optional sleeve member or sleeve 62 having a proximal end portion or extremity 62a and a distal end portion or extremity 62b. Sleeve or elongate tubular member 62 is made from any suitable material such as flexible plastic or metal and has a lumen extending longitudinally therethrough for receiving the needle 61. The sleeve 62 and the needle 61 are slidable relative to each other in a longitudinal direction. In this regard, tubular needle 61 is slidably disposed in sleeve 62 and movable from a retracted position in which the tubular needle is recessed within distal end portion 62b of sleeve to an extended position in which the needle 61 projects distally of the sleeve 62. Needle 61 and sleeve 62 can be slidably disposed within working channel 51 and side port 62 of insertion tube 31 and in one embodiment each have a length of at least approximately 34 centimeters and in another embodiment each have a length of at least approximately 44 centimeters so that when distal end portions 61b and 62b are extending from distal extremity 31b of the insertion tube 31 or otherwise in the vicinity of distal face 32, proximal end portions 61a and 62a are accessible at side port 52.

Figure 3:
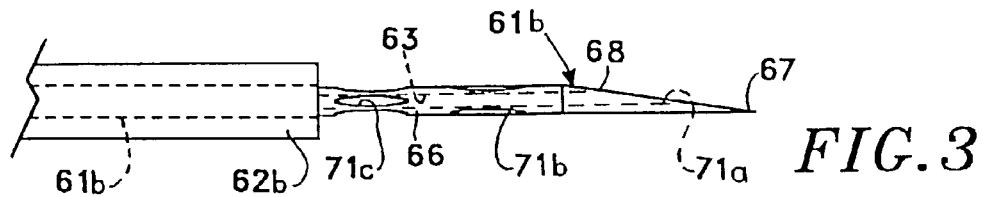
FIG. 3 is an enlarged side view of the distal portion of the apparatus of FIG. 1 taken along the line 3-3 of FIG. 1.

The hollow or tubular needle 61 has a passage 63 extending longitudinally therethrough from proximal end portion 61a to distal end portion 61b. The modified needle distal end portion 61b is made from any suitable material such as stainless steel and has a size ranging from 16 to 28 gauge and preferably ranging from 23 to 26 gauge. As shown most clearly in FIG. 3, the distal end portion 61b has a cylindrical wall 66 for forming internal passage 63 and also has a sharpened or beveled distal end 67 formed in part by a tapered end surface 68. At least one opening 71 is provided in distal end portion 61 and can include or consist of an opening 71a provided in tapered end surface 68. As an alternative to or in addition to opening 71a, at least one and as shown a plurality of openings 71 can be provided in cylindrical wall 66. A plurality of two openings 71b and two additional openings 71c are provided in wall 66. Openings 71b are diametrically disposed relative to each other, so as to be 180° apart, and openings 71c are also diametrically disposed relative to each other but offset 90° from openings 71b. The openings 71c are spaced longitudinally behind the openings 71b. Openings 71b and 71c can be any suitable shape or size and are shown as being elongate or oblong in shape. It should be appreciated that a needle distal end portion 61b having only openings 71b or openings 71c can be provided and be within the scope of the present invention. In one embodiment of needle 61, tapered surface 68 is closed and openings 71 provided only in cylindrical wall 66. Needle proximal end portion 61a and the central portion of needle 61 can be made from plastic, metal or any other suitable material.

Figure 4:
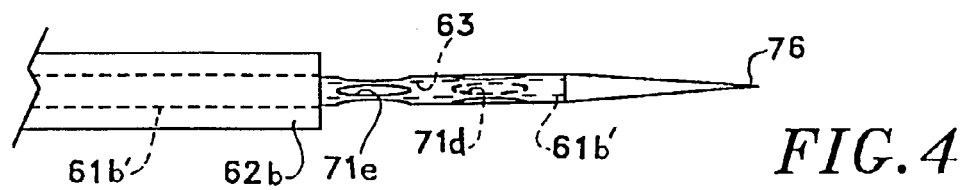
FIG. 4 is an enlarged side view, similar to FIG. 3, of the distal portion of another embodiment of the apparatus for treating gastroesophageal reflux disease of the present invention.

Another embodiment of the modified distal end portion of the needle 61 is shown in FIG. 4. Distal end portion 61b' therein has a sharpened or pointed distal end 76 which is generally conical in shape. No opening 71 is provided in the closed pointed end 76. A plurality of three circumferentially-disposed openings 71d are provided in cylindrical wall 66 proximal of pointed end 76. Openings 71d are circumferentially spaced apart at separation angles of approximately 120°. A second set of three openings 71e extend through cylindrical wall 66 proximal of openings 71d. Openings 71e are also circumferentially spaced apart at separation angles of approximately 120°. The openings 71e are angularly offset about the centerline of distal end portion 61b' relative to the opening 71d.

A fluid connector 81 is secured or coupled to proximal end portion 61a of needle 61 and a gripping member or grip 82 is secured to the proximal end portion 62a of the sleeve 62 (see FIG. 1). Fluid connector 81 includes first and second luer fitting portions 83 and 84, or any other suitable fitting portions, which communicate with passage 63 in needle 61. First luer fitting portion 83 is capped in FIG. 1. Fluid connector 81 and grip 82 are longitudinally movable relative to each other so as to cause relative longitudinal movement between needle 61 and sleeve 62. More specifically, grip 82 can be slid forwardly and rearwardly on proximal end portion 61a of the needle 61 relative to fluid connector 81. Movement of grip 82 forwardly relative to fluid connector 81 causes distal end portion 62b of sleeve 62 to extend fully over distal end portion 61b of the needle 61 so that the needle has fully retracted within sleeve 62. Conversely, movement of grip 82 rearwardly relative to fluid connector 81 causes sleeve distal end portion 62b to retract relative to needle distal end portion 61b so as to expose the needle distal end portion 61b.

The handle means of treatment device 21 includes supply assembly 27 coupled to proximal extremity 31a of insertion tube 31 (see FIG. 1). More specifically, supply assembly 27 is secured to the proximal extremity of needle assembly 26. The supply assembly 27 is included within the means of treatment device 21 for introducing a liquid or solution through passage 63 of needle 61 and out one or more of the openings 71 provided in the needle distal end portion 61b. Supply assembly 27 comprises a conventional syringe or first syringe 91 having a reservoir or barrel 92 provided with any suitable fitting portion such as luer fitting portion 93 at the forward end thereof and a plunger 94 for dispelling liquid within barrel 92 through luer fitting portion 93. The supply assembly 27 further includes second and third reservoirs in the form of second and third syringes 96 and 97. The second syringe 96 is filled with dimethyl sulfoxide (DMSO) or any other suitable liquid. The third syringe 97 is filled with a saline solution or any other suitable aqueous or physiologic solution.

A manifold assembly or manifold 98 is provided for coupling syringes 91, 96 and 97 to fluid connector 81. In one embodiment, the manifold 98 has a plurality of three stop cocks 101-103 and a plurality of at least two and as shown a plurality of four ports or luer fitting portions. A first luer fitting portion 104 cooperatively mates with the forward luer fitting portion 93 of syringe 91. A second luer fitting portion 106 cooperatively mates with second luer fitting portion 84 of the fluid connector 81. Third and fourth luer fitting portions 107 and 108 are additionally provided. The third luer fitting portion 107 is connected by a tube 109, a portion of which is shown in FIG. 1, to second syringe 96 and the fourth luer fitting portion 108 is connected by a tube 110, a portion of which is shown in FIG. 1, to third syringe 97. The stop cocks 101-103 operate in a conventional manner to direct fluid flow between the luer fitting portions 104 and 106-108. In a further embodiment of the invention (not shown), syringe 91 can be secured directly to fluid connector 81 or the proximal end portion 61a of needle 61. It should be appreciated that manifold 98 can alternatively be provided with less than or greater than four luer fitting portions or be of any other configuration for coordinating fluid flow from a plurality of syringes or other fluid reservoirs.

Figure 5:
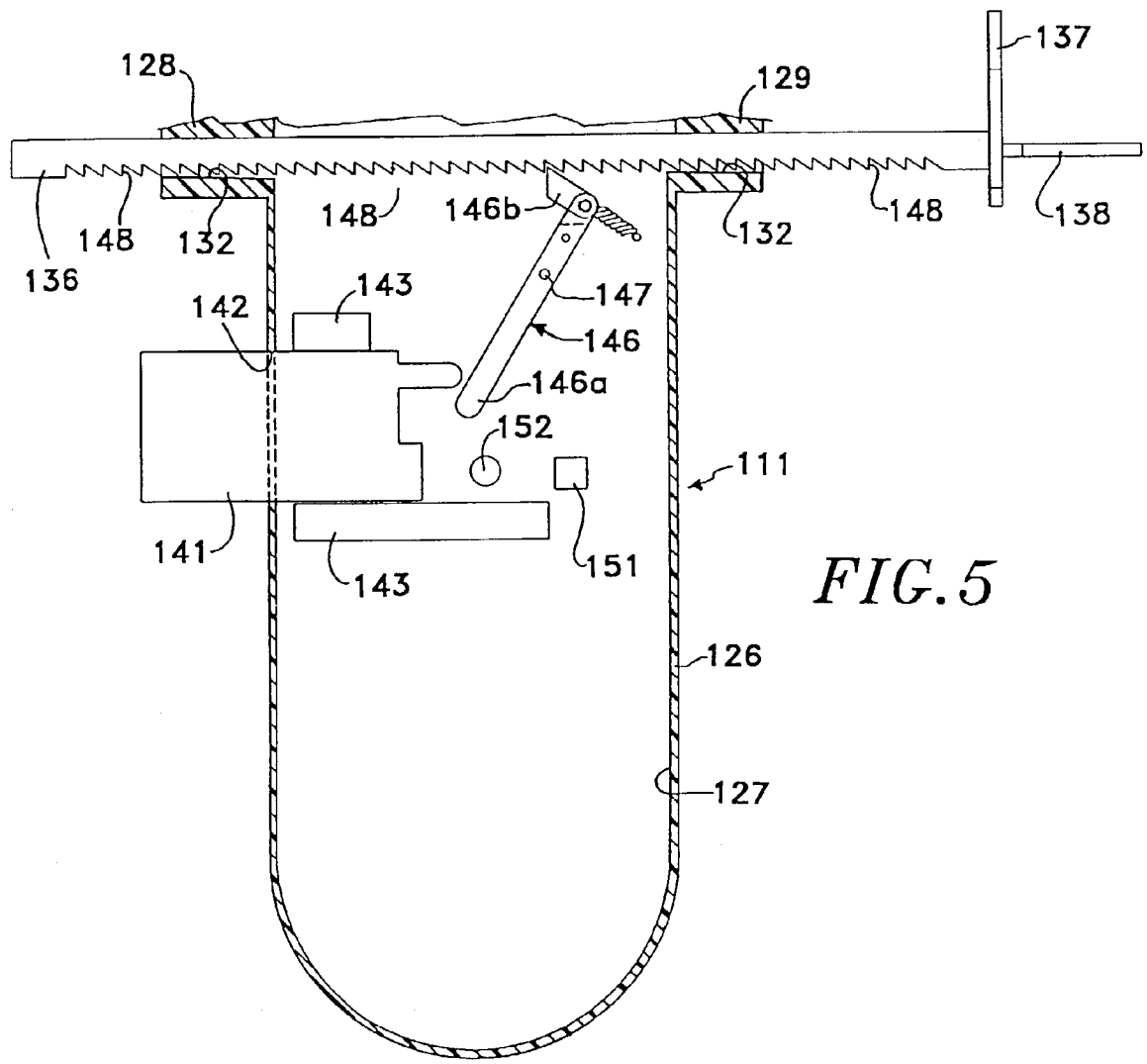
FIG. 5 is a cross-sectional view of a proximal portion of the apparatus of FIG. 1 taken along the line 5-5 of FIG. 1.

Supply assembly 27 further includes a delivery device or gun 111 for supplying a plurality of discrete preselected amounts of the fluid within barrel 92 to needle 61 (see FIGS. 1 and 5). Gun 111 has a cylindrical housing 112 made from plastic or any other suitable material for receiving syringe barrel 92. Housing 112 is formed from a base portion 113 and a cover portion 114 pivotally secured to the base portion 113 by hinge 116. A latch 117 is pivotally coupled to the cover portion 114 for engaging base portion 113 and thereby locking the cover portion 114 in a closed position. Housing 112 has a forward opening 118 for receiving luer fitting portion 93 of the syringe 91. A handle 126 made from plastic or any other suitable material depends from base portion 113. The handle 126 has an internal cavity 127. First and second spaced-apart reinforcing members 128 and 129 extend downwardly from the base portion 113 at the front and rear of handle 126. The reinforcing members 128 and 129 are longitudinally aligned and each provided with a bore 132 extending longitudinally therethrough and opening into internal cavity 127. A rod 136 made from plastic or any other suitable material is slidably disposed within bores 132. The rod 136 has a paddle 137 extending upwardly from the rear thereof perpendicularly to the longitudinal axis of the rod. Paddle 137 is adapted to engage the end of syringe plunger 94. A ring 138 sized for receiving a finger of a human hand extends rearwardly from paddle 137 for facilitating the pulling of rod 136 rearwardly in bores 132.

Rod 136 and paddle 137 are included within the finger operable means of gun 111 for causing incremental relative movement between barrel 92 and plunger 94 of the syringe 91. A trigger 141 extends from an opening 142 at the front of handle 126 below rod 136. The trigger is slidably disposed in a direction parallel to the longitudinal axis of rod 136 between first and second spaced-apart guides 143 provided in internal cavity 127. Trigger 141 moves between a first or fully extended position to a second or fully retracted position. A lever 146 is pivotally coupled to handle 126 by means of a pin 147. The lever 146 has a first end portion 146a which extends behind trigger 141 and a second end portion 146b having a wedge-like shape for engaging one of a plurality of longitudinally spaced-apart notches formed in the bottom of rod 136. When trigger 141 is pulled rearwardly by the finger of a human hand, the trigger engages lever first end portion 146a to cause the lever 146 to pivot about pin 147 from a first or home position to a second or operational position. Lever second end portion 146b moves forwardly during this half-stroke to engage one of notches 148 and cause the rod 136 to move forwardly relative to housing 112. The paddle 137 follows rod 136 and incrementally pushes plunger 94 into barrel 92 for each pull of trigger 141.

A fixed stop 151 is provided in handle 126 for limiting the rearward movement of trigger 141 and thus determining the incremental amount of fluid within barrel 92 dispelled from the syringe 91 with each pull of trigger 141. The rearward travel of trigger 141 can be selectively limited by means of one or more additional pins or stops 152, one of which is shown in FIG. 5. Adjustable limit pin 152 is slidably mounted within handle 126 for movement from a first position out of the path of trigger 141 to a second position within the path of the trigger 141 so as to selectively limit the rearward stroke of trigger 141 when engaged and placed in its second position.

A coil spring 156 or any other suitable biasing number having one end coupled to a pin 157 mounted within handle 126 and a second end secured to the second end portion 146b of lever 146 is provided. Spring 156 urges lever 146 back to its home position, out of engagement with notches 148, when the finger pressure on trigger 141 is released. Spring 156 causes lever first end portion 146a to push trigger 141 outwardly from opening 142 to its home position.

A finger operable adjustment mechanism 166 is connected to needle proximal end portion 61a and sleeve proximal end portion 62a for causing longitudinal relative movement between the needle 61 and the sleeve 62. The adjustment mechanism 166 can be of any suitable type for use with any suitable needle assembly having a needle and sleeve which are adjustable relative to each other. One embodiment of such an adjustment mechanism 166 is carried by gun 111. As shown in FIG. 1, such adjustment mechanism 166 has a first or forward post 167 and a second or rear post 168 extend upwardly from the top of cover portion 114. The longitudinally spaced-apart posts 167 and 168 extend perpendicularly to barrels 92. A slidable member or slide bar 171 is slidably mounted in a bore (not shown) provided in forward post 167 for forward and rearward movement in a direction parallel to barrel 92. A thumb screw 172 having an enlarged head 172a is slidably disposed in a bore (not shown) provided in rear post 168. Screw head 172a abuts rear post 168 and the other end of screw 172 is threadably received within the back end of slide bar 171. Counterclockwise rotation of thumb screw 172 relative to rear post 168 causes slide bar 171 to move rearwardly toward forward post 167, while clockwise rotation of the thumb screw 172 results in the slide bar 171 moving forwardly away from post 167. An L-shaped coupler 173 is pivotally coupled to the forward end of slide bar 171 by means of a pin 174. The coupler 173 has first and second spaced-apart arms 176 forming a slot 178 therebetween for receiving the central portion of grip 82. A screw 179 extends between the arms 176 for locking the arms to grip 82 and thus longitudinally locking sleeve 62 relative to needle 61.

Treatment device 21 can be used for any suitable procedure such as the treatment of gastroesophageal reflux disease (see FIGS. 6-12). A portion of a human body 184 is shown in FIGS. 6-8 and has an internal cavity in the form of esophagus 186 extending through a lower esophageal sphincter 187 to a stomach 188. Such cavity is accessible by a natural body opening in the form of mouth 192 and is defined by a wall 193. Esophagus 186 is part of the gastrointestinal tract of body 184 that extends from mouth 192 to an anus (not shown in FIGS. 6-8). The esophageal mucosa 196 serves as the inner layer of the intraluminal wall 193 in the esophagus 186 and the gastric mucosa 197 serves as the inner layer of the intramural wall 193 in the stomach 188. The esophageal mucosa and the gastric mucosa meet at the squamous columnar junction 198. Wall 193 further includes a muscle layer comprising layer of circular muscle 201 extending beneath mucosa layers 196 and 197 and layer of longitudinal muscle 202 beneath circular muscle 201. The muscle layers 201 and 202 each extend around the esophagus 186 and the stomach 188. A submucosal space 203 is any space located between mucosa layer 196 or 197 and circular muscle layer 201 created by the separation of layer 196 or 197 from muscle layer 201. The wall 193 has a depth or thickness which includes at least mucosa layers 196 and 197, muscle layers 201 and 202 and the submucosal space 203. The phreno-esophageal ligament 204 and diaphragm 206 extend around the esophagus 186 above the lower esophageal sphincter 187. In the vicinity of the lower esophageal sphincter, as that term is used herein, includes at least the lower third of the esophagus, the squamous columnar junction 198, and the gastric cardia or upper portion of the stomach 188.

The apparatus of the present invention optionally includes a balloon assembly 211 made from any suitable material such as polyethylene, latex rubber, silicone or polyolefin (see FIGS. 6 and 7). Balloon assembly 211 has a first or lower balloon 212 sized for disposition below the lower esophageal sphincter 187 and is shown sized for disposition in stomach 188 where the esophagus 186 enters the stomach. Balloon assembly 211 has a second or upper balloon 213 sized for disposition in esophagus 186 above the lower esophageal sphincter 187. An opening 214 can be provided through upper balloon 213 for permitting insertion tube 31 to extend through the balloon 213. Opening 214 is sized relative to insertion tube 31 so as to snugly engage the insertion tube when upper balloon 213 is inflated. An inflation tube 216 extends from upper balloon 213 out of the esophagus 186 and mouth 192 for permitting inflation of the balloons 212 and 213. A connecting tube extends between lower and upper balloons 212 and 213 for permitting lower balloon 212 to be inflated by means of inflation tube 216. In an alternate embodiment of balloon assembly 211, lower balloon 212 can be separate from upper balloon 213 in which case each of the balloons is provided with a separate inflation tube.

In a method of the present invention, an inert, nonresorbable material is introduced into the body 184 to augment the wall of a hollow viscus in the body. In the embodiments of the method discussed below, this material is introduced into wall 193 of the gastrointestinal tract in the vicinity of the lower esophageal sphincter 187 so as to augment the wall and thus treat gastroesophageal reflux disease. Although any suitable material can be used with the method and/or apparatus of the present invention, one such material is at least one solution which when introduced into the body forms a nonbiodegradable solid. As used herein, a solid means any substance that does not flow perceptibly under moderate stress, has a definite capacity for resisting forces which tend to deform it (such as compression, tension and strain) and under ordinary conditions retains a definite size and shape; such a solid includes, without limitation, spongy and/or porous substances. One such embodiment of the at least one solution is first and second solutions which when combined in the body form the nonbiodegradable solid. Another such embodiment is a nonaqueous solution which can be introduced into the body as a liquid and from which a solid thereafter precipitates. A preferred embodiment of such a nonaqueous or augmenting solution is a solution of a biocompatible polymer and a biompatible solvent which can optionally include a contrast agent for facilitating visualization of the solution in the body.

A particularly preferred augmenting or bulking solution is a composition comprising from about 2.5 to about 8.0 weight percent of a biocompatible polymer, from about 52 to about 87.5 weight percent of a biocompatible solvent and optionally from about 10 to about 40 weight percent of a biocompatible contrast agent having a preferred average particle size of about 10 μm or less. It should be appreciated that any percents stated herein which include a contrast agent would be proportionally adjusted when the contrast agent is not utilized. Any contrast agent is preferably a water insoluble biocompatible contrast agent. The weight percent of the polymer, contrast agent and biocompatible solvent is based on the total weight of the complete composition. In a preferred embodiment, the water insoluble, biocompatible contrast agent is selected from the group consisting of barium sulfate, tantalum powder and tantalum oxide. In still a further preferred embodiment, the biocompatible solvent is dimethylsulfoxide (DMSO), ethanol, ethyl lactate or acetone.

The term "biocompatible polymer" refers to polymers which, in the amounts employed, are non-toxic, chemically inert, and substantially non-immunogenic when used internally in the patient and which are substantially insoluble in physiologic liquids. Suitable biocompatible polymers include, by way of example, cellulose acetates (including cellulose diacetate), ethylene vinyl alcohol copolymers, hydrogels (e.g., acrylics), poly($C_1$-$C_6$) acrylates, acrylate copolymers, polyalkyl alkacrylates wherein the alkyl and alk groups independently contain one to six carbon atoms, polyacrylonitrile, polyvinylacetate, cellulose acetate butyrate, nitrocellulose, copolymers of urethane/carbonate, copolymers of styrene/maleic acid, and mixtures thereof. Copolymers of urethane/carbonate include polycarbonates that are diol terminated which are then reacted with a diisocyanate such as methylene bisphenyl diisocyanate to provide for the urethane/carbonate copolymers. Likewise, copolymers of styrene/maleic acid refer to copolymers having a ratio of styrene to maleic acid of from about 7:3 to about 3:7. Preferably, the biocompatible polymer is also non-inflammatory when employed in situ. The particular biocompatible polymer employed is not critical and is selected relative to the viscosity of the resulting polymer solution, the solubility of the biocompatible polymer in the biocompatible solvent, and the like. Such factors are well within the skill of the art.

The polymers of polyacrylonitrile, polyvinylacetate, poly ($C_1$-$C_6$) acrylates, acrylate copolymers, polyalkyl alkacrylates wherein the alkyl and alk groups independently contain one to six carbon atoms, cellulose acetate butyrate, nitrocellulose, copolymers of urethane/carbonate, copolymers of styrene/maleic acid and mixtures thereof typically will have a molecular weight of at least about 50,000 and more preferably from about 75,000 to about 300,000.

Preferred biocompatible polymers include cellulose diacetate and ethylene vinyl alcohol copolymer. In one embodiment, the cellulose diacetate has an acetyl content of from about 31 to about 40 weight percent. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the implanting properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 8 weight-volume percent of the ethylene vinyl alcohol copolymer in DMSO has a viscosity equal to or less than 60 centipoise at 20° C. and more preferably 40 centipoise or less at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution. In a particularly preferred embodiment, the copolymers employed herein comprise a mole percent of ethylene of from about 25 to about 60 and a mole percent of vinyl alcohol of from about 40 to about 75, more preferably a mole percent of ethylene of from about 40 to about 60 and a mole percent of vinyl alcohol of from about 40 to about 60.

The term "contrast agent" refers to a biocompatible (nontoxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. The term "water insoluble contrast agent" refers to contrast agents which are insoluble in water (i.e., has a water solubility of less than 0.01 milligrams per milliliter at 20° C.) and include tantalum, tantalum oxide and barium sulfate, each of which is commercially available in the proper form for in vivo use and preferably having a particle size of 10 μm or less. Other water insoluble contrast agents include gold, tungsten and platinum powders. Methods for preparing such water insoluble biocompatible contrast agents having an average particle size of about 10 μm or less are described below. Preferably, the contrast agent is water insoluble (i.e., has a water solubility of less than 0.01 mg/ml at 20° C.)

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, ethyl lactate, acetone, and the like. Aqueous mixtures with the biocompatible solvent can also be employed provided that the amount of water employed is sufficiently small that the dissolved polymer precipitates upon injection into a human body. Preferably, the biocompatible solvent is ethyl lactate or dimethylsulfoxide.

The term "encapsulation" as used relative to the contrast agent being encapsulated in the precipitate is not meant to infer any physical entrapment of the contrast agent within the precipitate much as a capsule encapsulates a medicament. Rather, this term is used to mean that an integral coherent precipitate forms which does not separate into individual components, for example into a copolymer component and a contrast agent component.

The compositions employed in the methods of this invention are prepared by conventional methods whereby each of the components is added and the resulting composition mixed together until the overall composition is substantially homogeneous. For example, sufficient amounts of the selected polymer are added to the biocompatible solvent to achieve the effective concentration for the complete composition. Preferably, the composition will comprise from about 2.5 to about 8.0 weight percent of the polymer based on the total weight of the composition and more preferably from about 4 to about 5.2 weight percent. If necessary, gentle heating and stirring can be used to effect dissolution of the polymer into the biocompatible solvent, e.g., 12 hours at 50° C.

Sufficient amounts of the contrast agent are then optionally added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 to about 35 weight percent. When the contrast agent is not soluble in the biocompatible solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, gamma irradiation, or electron beam induced polymerization employing, as necessary, a polymerization catalyst or polymerization initiator to provide for the polymer composition. The specific manner of polymerization is not critical and the polymerization techniques employed do not form a part of this invention. In order to maintain solubility in the biocompatible solvent, the polymers described herein are preferably not cross-linked.

In another particularly preferred embodiment of the augmenting solution, the biocompatible polymer composition can be replaced with a biocompatible prepolymer composition containing a biocompatible prepolymer. In this embodiment, the composition comprises a biocompatible prepolymer, an optional biocompatible water insoluble contrast agent preferably having an average particle size of about 10 μm or less and, optionally, a biocompatible solvent.

The term "biocompatible prepolymer" refers to materials which polymerize in situ to form a polymer and which, in the amounts employed, are non-toxic, chemically inert, and substantially non-immunogenic when used internally in the patient and which are substantially insoluble in physiologic liquids. Such a composition is introduced into the body as a mixture of reactive chemicals and thereafter forms a biocompatible polymer within the body. Suitable biocompatible prepolymers include, by way of example, cyanoacrylates, hydroxyethyl methacrylate, silicon prepolymers, and the like. The prepolymer can either be a monomer or a reactive oligomer. Preferably, the biocompatible prepolymer is also non-inflammatory when employed in situ.

Prepolymer compositions can be prepared by adding sufficient amounts of the optional contrast agent to the solution (e.g., liquid prepolymer) to achieve the effective concentration for the complete polymer composition. Preferably, the prepolymer composition will comprise from about 10 to about 40 weight percent of the contrast agent and more preferably from about 20 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm).

When the prepolymer is liquid (as in the case of polyurethanes), the use of a biocompatible solvent is not absolutely necessary but may be preferred to provide for an appropriate viscosity in the augmenting solution. Preferably, when employed, the biocompatible solvent will comprise from about 10 to about 50 weight percent of the biocompatible prepolymer composition based on the total weight of the prepolymer composition. When a biocompatible solvent is employed, the prepolymeric composition typically comprises from about 90 to about 50 weight percent of the prepolymer based on the total weight of the composition.

In a particularly preferred embodiment, the prepolymer is cyanoacrylate which is preferably employed in the absence of a biocompatible solvent. When so employed, the cyanoacrylate adhesive is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

Specific embodiments of augmenting solutions suitable for use in the apparatus and methods of the invention are described in U.S. Pat. No. 5,667,767 dated Sep. 16, 1997, U.S. Pat. No. 5,580,568 dated Dec. 3, 1996 and 5,695,480 dated Dec. 9, 1997 and International Publication Number WO 97/45131 having an International Publication Date of Dec. 4, 1997, the entire contents of which are incorporated herein by this reference.

In operation and use of treatment device 21 in the method of the present invention, syringe 91 is filled with the augmenting solution in preparation of the procedure. The syringe 91 is loaded into gun 111 by opening cover portion 114 to permit placement of barrel 92 within housing 112. Ring 138 is grasped to pull rod 136 rearwardly relative to housing 112 so that paddle 137 is disposed behind the retracted plunger 94. Cover portion 114 is closed and secured to base portion 113 by means of latch 117. The physician thereafter pulls trigger 141 as necessary to cause paddle 137 to engage the rear of plunger 94.

Although the method of the present invention permits supply assembly 27 to be attached to needle assembly 26 after needle 61 and sleeve 62 have been disposed in working channel 51 of probe 22, the method alternatively permits the supply assembly 26 to be attached to the needle assembly prior to such disposition of the needle assembly within probe 22. In either case, attachment is accomplished by coupling first luer fitting portion 104 of manifold 98 to luer fitting portion 93 of syringe 91 and second luer fitting portion 106 of the manifold to the first luer fitting portion 83 of fluid connector 81. Coupler 173 is pivoted downwardly so that first and second arms 176 thereof engage grip 82 and screw 179 tightened to secure the grip 82 in the slot 178 between arms 176. Thumb screw 172 is rotated in a counterclockwise direction relative to rear post 186 to ensure that needle 61 is fully retracted within sleeve 62. Thereafter, saline solution syringe 97 is coupled by means of tube 110 to third luer fitting portion 107 of the manifold 98 and DMSO syringe 96 is coupled by means of tube 109 to fourth luer fitting portion 108 of the manifold.

Probe 22 is prepared by connecting light cable 46 to light source 47 and attaching the proper eyepiece 41 to handle 33. In addition, all other conventional attachments are applied to the probe 22.

After the patient has been appropriately sedated or anesthetized, optional balloon assembly 211 is introduced through mouth 192 into esophagus 186 by standard procedures (not shown). In one method of so placing lower and upper balloons 212 and 213 in the esophagus, the lower balloon 212 is removably mounted on distal extremity 31b of the insertion tube 31 and the upper balloon 213 is annularly mounted about the insertion tube 31 proximal of the lower balloon. Probe handle 33 is grasped by the physician to introduce distal extremity 31b of probe 22 into mouth 192 and advance the insertion tube 31 down esophagus 186. Optical viewing device 23 facilities such advancement by the physician of insertion tube 31. In addition, optical viewing device 23 enables the physician to ensure that lower balloon 212 is properly disposed within esophagus 186. Insertion tube 31 has a length so that when distal extremity 31b is in the vicinity of lower esophageal sphincter 187, proximal extremity 31a is outside of body 184.

Balloon assembly 211 is thereafter inflated by means of inflation tube 216. Upper balloon 213 creates a substantially fluid-tight seal in the esophagus above the lower esophageal sphincter 187 and lower balloon 212 creates a substantially fluid-tight seal of the esophagus below the lower esophageal sphincter 187. Inflation tube 216 can optionally be used to hold lower balloon 212 in a position against the gastroesophageal juncture. Connecting tube 217 is longitudinally sized so that upper and lower balloons 213 and 212 are spaced-apart a distance ranging from 4 to 15 centimeters. Balloon assembly 211 serves to create an isolated or sealed space 221 bounded by upper and lower balloons 213 and 212 and substantially centered on lower esophageal sphincter 187. The additional passageway 56 in insertion tube 31 can be used to remove any liquids or other material within the sealed space 221. If then filled with air, such an air space 221 inhibits the precipitation of the augmenting solution before its injection into wall 193.

Distal end portions 61b and 62b of needle assembly 26 are now inserted through side port 52 of insertion tube 31 and advanced until such distal end portions of needle 61 and sleeve 62 are in the vicinity of insertion tube distal extremity 31b. Needle 61 and sleeve 62 are each movable from a first position in which distal end portions 61b and 62b are each retracted within insertion tube 31 and thus recessed within working channel 51 to a second position in which the distal end portions 61b and 62b extend distally beyond the end of insertion tube 31. The needle and sleeve each have a sufficient length so that the physician holding gun 111 can extend both the needle and the sleeve distally from distal extremity 31b a significant distance, should that be desired.

A portion of the procedure for augmenting wall 193 in the vicinity of lower esophageal sphincter 187 is shown in FIGS. 7 and 8. Under the guidance of optical viewing device 23, insertion tube distal extremity 31b is maneuvered to a position above the portion of wall 193 which is to be augmented. The physician retracts sleeve 62 relative to needle 61 by means of adjustment mechanism 166 so that needle distal end portion 61b extends beyond sleeve distal end portion 62b a selected amount of at least 2 millimeters and preferably ranging from 2 to 15 millimeters. Such amount of extension can be easily determined for example by correlating such extension as a function of the rotation of thumb screw 172 and properly calibrating the position of thumb screw 172 relative to rear post 168 in this regard. The retraction of needle 61 relative to sleeve 62 can occur either within working channel 51 or after the needle 61 and sleeve 62 have been extended from insertion tube distal extremity 31b. The physician primes needle 61 with the saline or other aqueous or physiologic solution from syringe 97 and ensures that needle passage 63 is filled with saline solution by observing with optical viewing device 23 the saline solution being dispelled from the one or more openings 71 in needle distal end portion 61b. For simplicity, the operation of conventional stop cocks 101-103 for directing appropriate fluids to and from needle passage 63 will not be discussed in connection with the procedure.

The physician causes sharpened end 67 of needle 61 to penetrate wall 193 by moving the needle 61 and sleeve 62 closer to side port 52. The field of view of optical viewing device 23 permits the physician to observe the penetration of wall 193. Although the needle 61 and sleeve 62 can penetrate the wall 193 at any angle, it is preferred that the angle of penetration relative to wall 193 be less than 90° and more preferably less than 40° so that needle distal end portion 61b extends beneath the mucosal layer of wall 193 and does not extend further into muscle layers 201 and 202 or beyond (see FIG. 7). Saline solution is injected into wall 193 to cause the esophageal mucosa 196 or gastric mucosa 197, as the case may be, to separate from circular muscle 201 and create an enlargement 226 in wall 193 having an internal space 227 filled with the saline solution. The amount of saline solution required to create space 227 can range from 0.25 to 10 cc and preferably range from 1 to 3 cc. After the creation of enlargement 226, the physician retracts needle 61 from space 227 and withdraws the remaining saline solution from passage 63 by means of pulling back the plunger on syringe 97 or by any other suitable method. The physician next cleanses needle passage 63 with DMSO from syringe 96 to ensure that the saline solution has been removed from passage 63. DMSO cleansing can be determined by observing a slight amount of DMSO being dispelled from needle distal end portion 61b. This cleansing step is enhanced by the introduction of the DMSO downstream of saline stop cock 103 and upstream of augmenting solution stop cock 101. The DMSO is now removed from passage 63 by withdrawing the plunger of syringe 96 or by any other suitable means. Removal of the saline solution from passage 63 and the cleansing of the passage with DMSO inhibits premature precipitation within syringe 91 of the biocompatible polymer in the augmenting solution from the DMSO in the augmenting solution. Needle passage 63 is next primed with the augmenting solution carried by syringe 91 until such solution is available at the openings 71 in needle distal end portion 61b.

The physician positions insertion tube distal extremity 31b in the esophagus and causes needle distal end portion 61b to penetrate the enlargements 226 and extend into the saline filled space 227. Thereafter, the physician pulls trigger 141 to cause the desired preselected amount of augmenting solution to be introduced through needle 61 extending through probe 22 and upper balloon 213 into space 227. The openings 71 in needle distal end portion 61b are positioned so that the augmenting solution is preferably introduced into the middle of space 227. The contrast agent within the augmenting solution permits the viewing of the augmenting solution by means of fluoroscopy. In addition, the introduction of the augmenting solution into wall 193 can be monitored transabdominally or transesophageally by ultrasound. The rate of injection of the augmenting solution into space 227 can range from 0.1 cc per minute to 10 cc per minute.

Figure 9:
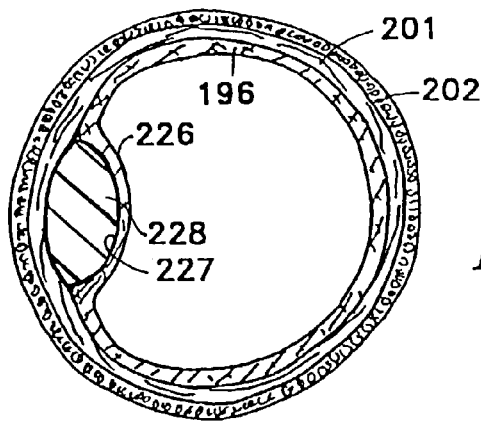
FIG. 9 is a cross-sectional view of the lower esophageal sphincter of FIG. 7 at the level of the gastric cardia taken along the line 9-9 of FIG. 7 showing partial coaptation of the esophagus from a method of the present invention.

Once the augmenting solution has been introduced into wall 193, the biocompatible polymer of the augmenting solution precipitates to form one or more discrete deposits or solid implants 228 (see FIGS. 7 and 9). The amount or bolus of augmenting solution injected into wall 193 for each implant can range from 0.05 cc to 10 cc. The ratio of augmenting solution to saline in space 227 can range from 2:1 to 1:8 and preferably range from approximately one part augmenting solution to two to three parts saline solution. In one embodiment, the space 227 created by the saline solution predefines the configuration of the precipitant or implant 228. As can be seen from FIG. 7, the discrete implant 228 shown therein occupies less than all of space 227. In another embodiment (not shown), more augmenting solution than saline is introduced into the wall 193 so that the discrete implant 228 more than fills the space 227 created by the saline.

It has been found that an injection of a suitable aqueous or physiologic solution such as a saline solution into wall 193 prior to the injection of the augmenting solution creates a space 227 which is more bulbous than elongate in configuration. The injection of the augmenting solution into the saline filled space 227 facilitates rapid precipitation and enhanced solidification of the biocompatible polymer. This rapid solidification facilitates the desired shaping of implant 228, which is shown in FIG. 7 as being somewhat spherical and elongated in shape. It has also been found that the saline solution facilitates the creation of a relatively soft and spongy implant 228. After completion of the injection of augmenting solution and the solidification of the biocompatible polymer, the remaining solution within space 227 disperses within body 184 and the space 227 contracts about implant 228 (see FIG. 8).

The injection of the saline solution into the wall 193 prior to the injection of the augmenting solution serves to condition or prepare the tissue in the wall 193, that is to help the wall 193 receive the augmenting solution and thus facilitate implantation of the biocompatible polymer. In this regard, the saline solution enhances the body's acceptance of the augmenting solution by minimizing the rejection response to the implant 228 and contributing to the body's healing response to the implant. The saline solution also enhances the resolution of any irritative or inflammatory reaction of the body to the DMSO. It should be appreciated that the invention is broad enough to cover any introduction of a solution into the tissue of the body to condition or prepare the tissue for treatment and thereafter performing a treatment on the tissue. Although the conditioning solution has been described as a saline solution, any suitable physiologic or aqueous solution can be used. In addition, antibiotics and/or anti-inflammatories can be introduced locally to condition the tissue.

The saline solution within space 227 also facilitates the rapid dispersion of the DMSO from the augmenting solution thus diluting any local irritant effect of the DMSO. The saline solution further acts as a heat sink for the heat of dissolution of the solvent.

Although only a single implant can be created in wall 193 in the method of the present invention, as shown in FIG. 9 where a single implant 228 is shown in wall 193 in the vicinity of the lower esophageal sphincter 187 and more specifically in the gastric cardia, additional implants 228 are created in wall 193 in one preferred embodiment of the method of the invention. In preparation thereof, needle 61 is removed from enlargement 226 and the augmenting solution within passage 63 withdrawn by pulling back on plunger 94. The needle 61 is cleansed with DMSO by filling the needle passage 63 with DMSO from syringe 96 and thereafter withdrawing the DMSO from the passage 63. After the subsequent priming needle passage 63 with saline solution from syringe 97, the procedure discussed above can be repeated to create such additional implants 228.

Figure 10:
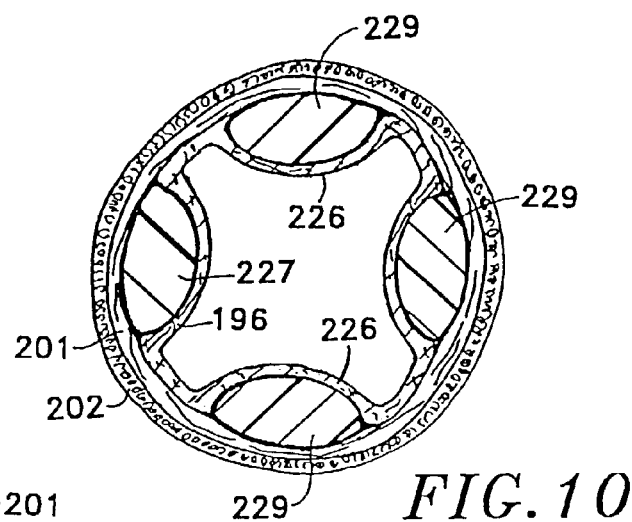
FIG. 10 is a cross-sectional view, similar to FIG. 9, of the lower esophageal sphincter showing partial coaptation of the esophagus from another method of the present invention.

The number and configurations of implants 228 formed in wall 193 can vary. In one embodiment of the method of the present invention, a plurality of circumferentially spaced-apart implants 229 are created in wall 193 below lower esophageal sphincter 187 and below squamous columnar junction (see FIGS. 7 and 10). Implants 229 are each somewhat pillow-like in shape and are disposed substantially in a plane extending perpendicularly to a longitudinal axis extending along the centerline of esophagus 186 and into the stomach 188. A rosette of four implants 229 is shown in FIG. 10. The implants 229 are spaced-apart around the center of the rosette at approximately 90° intervals. It should be appreciated, however, that less than four or greater than four implants 229 can be provided and formed in wall 193 and can be circumferentially spaced-apart at approximately equal angular intervals or asymmetrically disposed about the center line. The plane of implants can be disposed above, below and/or at the lower esophageal sphincter 187. In other embodiments, implants can be formed which are not disposed in a single plane.

Figure 11:
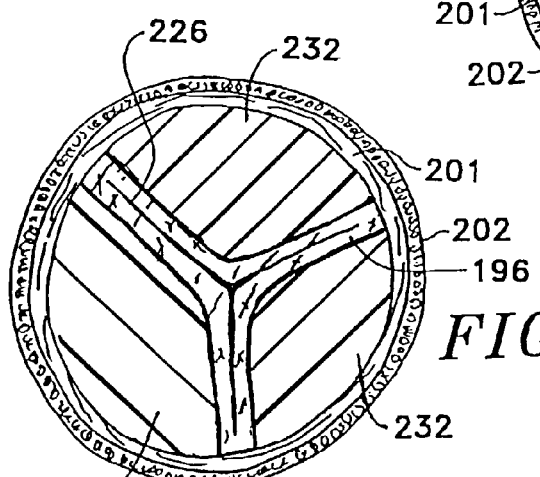
FIG. 11 is a cross-sectional view, similar to FIG. 9, of the lower esophageal sphincter showing complete coaptation of the esophagus from a further method of the present invention.

The sizing, spacing and configuration of implants determines whether esophagus 186 is partially coapted or completely coapted by the method of the present invention. Implants 229 in FIG. 10 are sized and circumferentially spaced so that the esophagus 186 is only partially coapted. In an alternate embodiment, a plurality of three circumferentially spaced-apart implants 232 are shown in FIG. 11 which result in complete coaptation of the esophagus 186. Less than three or more than three implants can alternatively be provided for completely coapting the esophagus 186.

Figure 12:
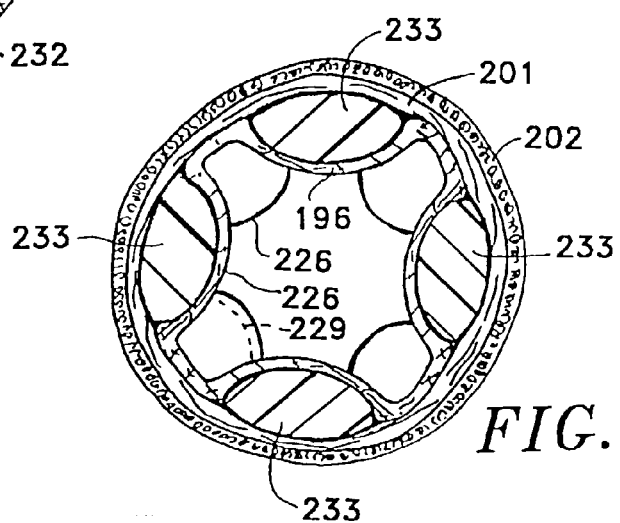
FIG. 12 is a cross-sectional view of the lower esophageal sphincter taken along the line 12-12 of FIG. 7 showing partial coaptation in two spaced apart positions of the esophagus after completion of yet a further method of the present invention.

In another embodiment of the method of the present invention, a plurality of implants disposed in additional planes spaced-apart from the first plane can be created. In FIG. 12, a second plurality of implants 233 is shown as having been created in wall 193 above the lower esophageal sphincter 187 and the plane of implants 229. A plurality of four implants 223, each sized and shaped substantially similar to implants 229, are shown in FIG. 12. The implants 233 are circumferentially spaced-apart at approximately 90° intervals and are offset approximately 45° from implants 229 in the lower plane. It should be appreciated that implants 233 can be longitudinally aligned or otherwise configured with respect to implants 229. In addition, less than four or greater than four implants 223 can be provided, the number of implants 223 being greater than, equal to or less than the number of implants 229. In one embodiment of the invention, the implants formed thereby in multiple planes or otherwise are disposed within a longitudinal range which approximates two centimeters. Such an array of implants can be longitudinally centered on the squamous columnar junction 198. In another embodiment, a single implant can be provided for augmenting or partially or completely coapting esophagus 186 in the vicinity of the lower esophageal sphincter.

Figure 13:
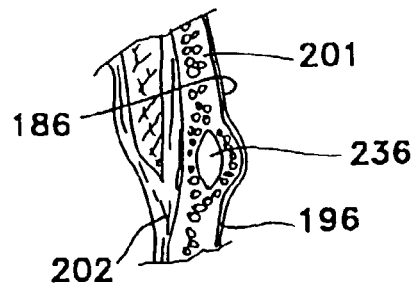
FIG. 13 is a cross-sectional view, similar to FIG. 8, of the lower esophageal sphincter showing augmentation and/or coaption of the esophagus from another method of the present invention.

In a further embodiment of the method of the present invention, one or more implants can be formed in portions of the wall 193 other than mucosal layers 196 and 197 to bulk the wall 193 in the vicinity of the lower esophageal sphincter 187. For example, as shown in FIG. 13, one or more implants 236 can be formed in one or both of muscle layers 201 and 202. An exemplary implant 236 is shown in FIG. 13 as being formed in circular muscle layer 201. The one or more implants 236 can serve to augment or partially or completely coapt the esophagus in the vicinity of the lower esophageal sphincter 187. Such implants 236 can also serve to reduce the distensibility of the muscle in layers 201 and 202 so as to tighten, stiffen or decrease the compliance of the lower esophageal sphincter 187 and modify the lower esophageal sphincter to reestablish the reflux barrier. In addition, the natural healing process around the implants 236, which includes fibrosis in the muscle layers, may further restrict opening of the muscle at the lower esophageal sphincter 187. Implants 236 can be arranged in a variety of configurations, including the various configuration of implants described above.

The implants created by the method and apparatus of the invention add bulk to the wall 193 so as to form a barrier between the stomach and the esophagus and reduce the distensibility of the muscle in layers 201 and 202 so as to increase the resistance of the wall 193 in the vicinity of the lower esophageal sphincter 187. The soft pillow-like implants interact with each other in a gentle fashion to permit food to travel down the esophagus. When the esophagus is at rest, the implants are close enough together to preclude retrograde travel of material in the stomach.

The implants hereof are advantageously formed between the mucosal layers 196 or 197 and muscle layers 202 and 203 of wall 193 or in the muscle layers 202 and 203 so as to not interfere with the blood flow and nourishment of such mucosal layers. Formation of implants which are too superficial in the wall 193 can interrupt the blood flow to the mucosa thereby causing the layer of the mucosa forming space 227 to eventually die and slough off. The injection of the augmenting material as a solution permits a relatively small needle 61 to be utilized.

Although the method of the invention has been described as including the formation of a space 227 by a saline solution injected into the wall 193 prior to an injection of augmenting solution into the wall 193, it should be appreciated that space 227 can be formed by other aqueous or physiologic solutions or by a local anesthetic. Alternatively, the augmenting solution can be injected into wall 193 without the prior formation of a space 227 by an injection of saline solution or otherwise. The augmenting solution can also be injected directly into the wall 193 without an injection of saline or any other solution for any secondary purpose described herein or otherwise. A saline or other aqueous or physiologic solution can optionally be introduced into such a space formed by the augmenting solution, that is after the introduction of the augmenting solution into the wall 193, to facilitate dispersion of the DMSO or other biocompatible solvent present in the augmenting solution. It can thus be seen that the invention is broad enough to cover the introduction of any conditioning solution into the tissue after the treatment to facilitate the treatment. In an alternative method for forming a plurality of implants within wall 193, a plurality of spaces 227 can be formed by saline solution from syringe 97. Subsequently, the augmenting solution from syringe 91 can be sequentially injected into each of such spaces.

In addition to or as an alternative to the prior or subsequent introduction of a saline or other solution into wall 193, the sealed space 221 formed by lower and upper balloons 212 and 213 can be filled with such an aqueous solution such as saline or water to facilitate the method of the present invention. A saline solution in the isolated space 221 can serve to disperse the DMSO and cure the one or more implants 228.

It should be appreciated that the implants of the present invention can be used as delivery vehicles for other materials such as radio isotopes, chemotherapeutic agents, anti-inflammatory agents and/or antibiotics. In addition, treatment device 21 can be used for introducing other materials, such as suspensions and the contrast agent, into a body and more specifically into a wall such as wall 193 in the body.

The contrast agent in the implants permits the implants to be monitored after completion of the procedure described above. Thus the stability of the implant and its configuration can be observed over time. Further procedures can be performed to supplement previously formed implants.

The implants of the invention can be removed for reversing the procedure of the invention. In one method for removing an implant, needle distal end portion 61b is inserted into the implant by means of probe 22 in a procedure similar to that discussed above. DMSO or any other suitable biocompatible solvent is injected from openings 71 to dissolve or partially dissolve the implant and thereafter the reformed augmenting solution is removed by means of needle passage 63. Alternatively, the mucosal layer forming the enlargement 226 can be incised to release the implant therein from wall 193. DMSO can optionally be sprayed on the implants to facilitate the removal thereof. The treatment of the invention can also be reversed by expanding the augmented or coapted region created by the implants in an suitable manner such as by use of a balloon or bougie.

Figure 14:
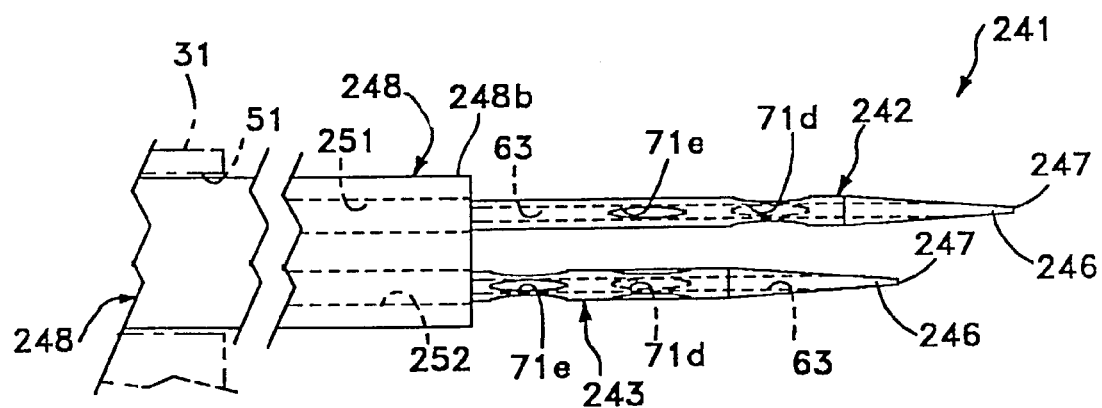
FIG. 14 is an enlarged side elevational view, similar to FIG. 4, of the distal portion of another embodiment of the apparatus for treating gastroesophageal reflux disease of the present invention.

In another embodiment of the needle assembly of the present invention, needle 61 can be provided with a plurality of lumens or passages extending longitudinally therethrough for permitting multiple liquids to be separately carried by the needle. In a further alternative embodiment, a plurality of needles can be introduced through the working channels of any suitable probe such as probe 22. Each of such needles can be used to perform one or more of the steps of the invention. For example, separate needles can be provided for the introduction of the saline solution or other physiologic or aqueous solution, for the introduction of the DMSO or other biocompatible solvent and for the introduction of the augmenting solution. A portion of a needle assembly 241 having a plurality of needles is shown in FIG. 14.

More specifically, needle assembly 241 has first and second needles 242 and 243, each of which is substantially similar to needle 61 shown in FIG. 4. Like reference numerals have been used to describe like components of needle 61 and first and second needles 242 and 243. Each of first and second needles 242 and 243 has a proximal end portion (not shown) and a sharpened distal end portion 246 provided with a distal opening 247. In alternate embodiments (not shown), any of the variety of needles described above can be utilized in needle assembly 241.

Needle assembly 241 further includes a sleeve member or sleeve 248 substantially similar to sleeve 62. Sleeve 248 has a proximal end portion (not shown) and a distal end portion 248b. The cylindrical sleeve 248 is provided with a plurality of lumens extending longitudinally therethrough, namely first and second spaced-apart lumens 251 and 252. First and second needles 242 and 243 are respectively disposed in first and second lumens 251 and 252 for slidable movement therein.

Sleeve 248 and first and second needles 242 and 243 carried thereby are slidably disposed within working channel 51 of probe 22 so that the proximal end portions of the first and second needles 242 and 243 and sleeve 248 are accessible at side port 52 on the probe 22. The proximal end portions of the first and second needles 242 and 243 are secured together by any suitable means such that the first and second needles are fixed longitudinally relative to each other and thus slide in unison within the sleeve 248. In the illustrated embodiment, the distal end of second needle 243 is spaced longitudinally from the distal end of first needle 242 and, more specifically, is spaced proximally of the distal end of the first needle a distance ranging from one to three millimeters. In an alternate embodiment, the distal ends of the first and second needles 242 and 243 can be positioned head-to-head, that is not longitudinally spaced apart. In such an embodiment, the needles can be spaced so closely together so as to resemble a single sharpened needle with a dual lumen. Alternatively, first and second needles 242 and 243 can be longitudinally fixed relative to each other by means of sleeve 248. In such an alternative embodiment, the needles 242 and 243 are also fixed relative to the sleeve 248.

The proximal end portions of first and second needles 242 and 243 are coupled to supply assembly 27 of treatment device 21. In one embodiment, first needle 242 is coupled to syringe 97 having saline solution therein and second needle 243 is coupled to syringe 91 having the augmenting solution therein.

In operation and use, needle assembly 241 is utilized in treatment device 21 in substantially the same manner as discussed above with respect to needle assembly 26. After insertion of sleeve 248 and needles 242 and 243 into working channel 51 and advancement of insertion tube distal extremity 31b through esophagus 186 to the vicinity of the lower esophageal sphincter 187, sleeve 248 is retracted relative to first and second needles 242 and 243 and the needles extended out from working channel 51. The needles are advanced toward wall 193 so that the sharpened distal end portion 246 of the distally-disposed first needle 242 penetrates the wall 193. Thereafter, saline solution from syringe 197 is injected into the wall 193 to create a space or pocket 227. Further advancement of the first and second needles 242 and 243 causes the second needle 243 to penetrate the enlargement 226 formed by the saline pocket 227. The physician then injects the augmenting solution through the second needle 243 into the pocket 227 to create an implant of the type described above. It should be appreciated that first and second needles 242 and 243 can alternatively be introduced simultaneously into wall 193 and be within the scope of the present invention.

In an alternate procedure where it is desired to introduce the augmenting solution into wall 193 prior to the introduction of the saline solution, the reservoir 91 of augmenting solution is coupled to first needle 242 and the reservoir 97 of saline solution 97 is coupled to second needle 243. In such a procedure, first needle 242 is first introduced into wall 193 to form an implant therein. The sharpened distal end 246 of second needle 243 is thereafter introduced into the wall to inject an appropriate amount of the saline solution in the vicinity of the implant for the purposes described above. In a further embodiment (not shown) where the distal ends of the first and second needles 242 and 243 are not longitudinally spaced apart, the needles 242 and 243 can be introduced simultaneously into the wall 193.

The inclusion of first and second needles 242 and 243 in needle assembly 241 reduces the complexity of the procedure. Since the augmenting solution and saline solution are no longer introduced through the same needle, the DMSO priming step required when only a single needle is utilized for the injection of the saline solution and the augmenting solution is eliminated.

Figure 15:
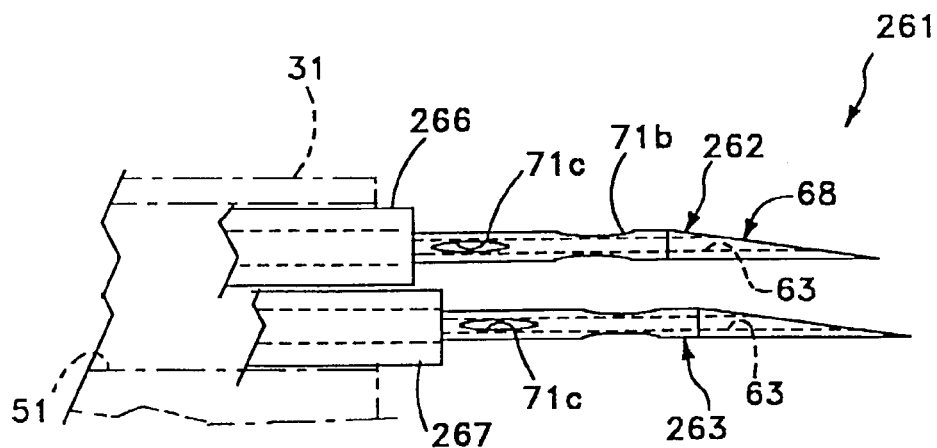
FIG. 15 is an enlarged side elevation view, similar to FIG. 5, of the distal portion of a further embodiment of the apparatus for treating gastroesophageal reflux disease of the present invention.

A further needle assembly for use with treatment device 21 and having a plurality of needles is shown in FIG. 15. Needle assembly 261 shown therein is substantially similar to needle assembly 26 and like reference numerals have been used to describe like components of needle assemblies 26 and 261. First and second needles 262 and 263 and first and second sleeves 266 and 267 are included in needle assembly 261. Each of the needles 262 and 263 is substantially identical to needle 61 shown in FIG. 3 and described above and each of the sleeves 266 and 267 is substantially similar to sleeve 62 described above. The first and second needles 262 and 263 are slidably disposed in respective longitudinally-extending lumens provided in first and second sleeve 266 and 267. As such, the first and second needles 262 and 263 are slidable relative to the respective first and second sleeves 266 and 267. In an alternate embodiment of the needle assembly 261, the first and second needles 262 and 263 can be fixed relative to respective first and second sleeves 266 and 267.

The first and second sleeves 266 and 267 are each disposed within working channel 61 for slidable movement relative to each other and insertion tube 31. The proximal end portions of the first and second needles 262 and 263 and the proximal end portions of the first and second sleeves 266 and 267 are each accessible at side port 52 for permitting control of the needles and sleeves relative to probe 22. Supply assembly 27 is coupled to the proximal end portions of each of the first and second needles 262 and 263. In this regard, first needle 262 is coupled to reservoir 91 of the augmenting solution and second needle 263 is coupled to reservoir 97 of the saline solution.

In operation and use, needle assembly 261 can be utilized in substantially the same manner as discussed above with respect to needle assemblies 26 and 241. In one such procedure, first needle 262 is used for introducing the augmenting solution into wall 193. Second needle 263 is used for introducing the saline solution into the wall 193. First and second needles 262 and 263 are movable relative to each other and to insertion tube 31 so as to permit the augmenting solution and the saline solution to be injected into wall 193 in any desired order.

Figure 16:
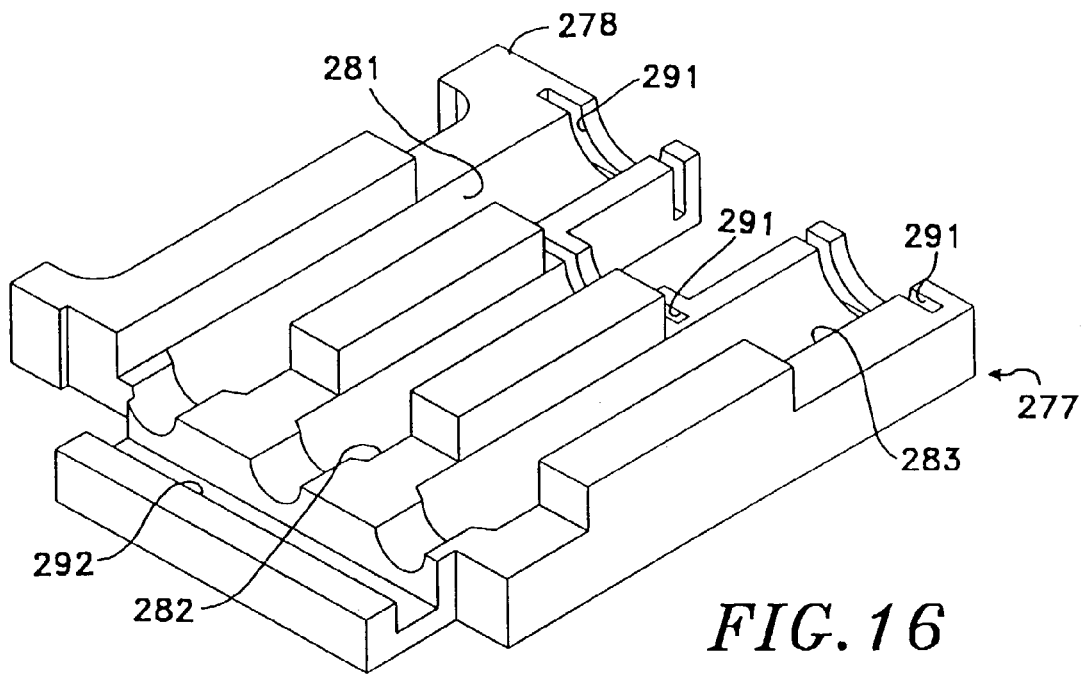
FIG. 16 is an isometric view of a portion of another embodiment of an apparatus for treating gastroesophageal reflux disease of the present invention.
Figure 17:
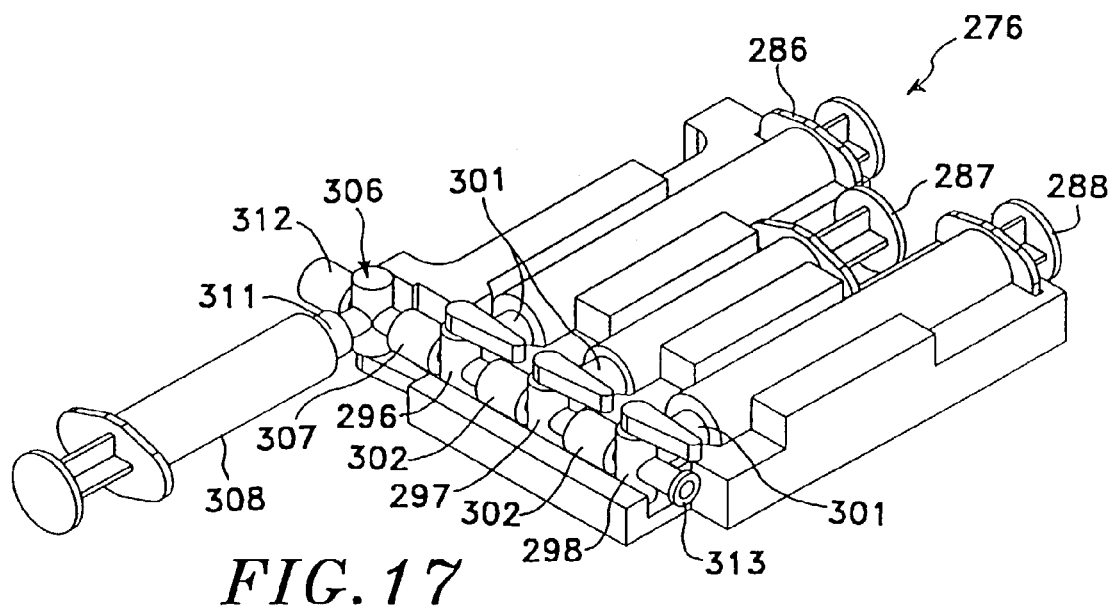
FIG. 17 is another isometric view of the apparatus of FIG. 16.

Another supply assembly for use with probe 22 and needle assemblies 26, 241 and 261 is shown in FIGS. 16-17. Supply assembly 276 shown therein includes a receptacle or manifold 277 for holding a plurality of syringes and stop cocks. The manifold 277 is formed from a body 278 made from any suitable material such as plastic. Body 278 is generally rectangular in shape and has a first side provided with a plurality of three cylindrical recesses 281-283 formed therein. Each of the recesses has a size and shape for receiving the barrel of a syringe. More specifically, the barrel of a first syringe 286 containing any suitable liquid such as the augmenting solution is disposed in first recess 281. The barrel of a second syringe 287 containing any suitable nonaqueous liquid such as DMSO is disposed in the second recess 282. The barrel of a third syringe 288 containing any suitable liquid such as an aqueous or physiologic solution is disposed in third recess 283. A slot 291 is provided in body 278 for each of the recesses. Each of the slots 291 extends across the respective recess and is sized and shaped to receive the flange formed on the plunger end of the respective syringe. Slots 291 serve to longitudinally lock the syringes within body 278.

Body 278 further includes a channel 292 for receiving a plurality of stop cocks 296-298. Each of such three-way stop cocks includes a suitable fitting such as luer fitting portion 301 for securing the stop cock to the respective syringe 286-288. Two additional fittings such as luer fittings 302 serve to connect second or DMSO stop cock 297 to first or augmenting solution stop cock 296 and second or saline solution stop cock 298.

A fourth three-way stop cock 306 is secured to first stop cock 296 by any suitable means such as luer fitting 307. A fourth or vent syringe 308 is secured to fourth or vent stop cock 306 by any suitable means such as luer fitting 311. Vent stop cock 306 includes an additional fitting such as luer fitting portion 312 for coupling supply assembly 276 to the needle assembly of treatment device 21. With respect to needle assembly 26, luer fitting portion 312 can secure to either first or second luer fitting portions 83 and 84 of fluid connector 81. Third stop cock 298 includes an additional luer fitting portion 313 which is capped during operation of supply assembly 276. Luer fitting portion 313 is shown as being uncapped in FIG. 17.

In operation and use, supply assembly 276 can be used in any of the procedures discussed above. In one exemplary procedure, the supply assembly 276 is coupled to fluid connector 81 of needle assembly 26. Second syringe 287 is filled with approximately ten cubic centimeters of DMSO and third syringe 288 is filled with approximately ten cubic centimeters of saline solution. The first syringe 286 is filled with approximately five cubic centimeters of the augmenting solution. Syringes 286-288 and stop cocks 296-298 and 306 are assembled and placed in manifold 277. Vent syringe 308 is connected to fourth stop cock 306. As shown in FIG. 17, saline solution syringe 288 is positioned in third recess 383 farthest from needle assembly 26, DMSO syringe 287 is placed in the second or middle recess 282 adjacent the saline solution syringe 288 and the augmenting syringe 286 is placed in the first recess 281 in a position closest to needle assembly 26.

Probe 22 is positioned in esophagus 186 of body 184 in the manner described above. After the supply assembly 276 is attached to fluid connector 21 of the needle assembly 26 by means of luer fitting portion 312, the physician confirms that needle 61 fully deploys and retracts relative to sleeve 62 without difficulty. Thereafter, the physician passes needle 61 and sleeve 62 down working channel 51 of probe 22 while visualizing the distal tip of needle assembly 26 by means of optical viewing device 23. In the manner discussed above, the physician punctures the mucosa in an appropriate location in the vicinity of the lower esophageal sphincter 187 and passes needle distal end portion 61b into the submucosal space 203. The physician slowly injects a sufficient quantity of the saline solution from third syringe 288 into wall 193 to create a generous submucosal space or pocket 227. After needle distal end portion 61b is removed from wall 193, the remaining saline solution within passage 63 of the needle 61 is removed by means of saline solution syringe 288. The retracted needle distal end portion 62b is retained in the field of view of optical viewing device 23 during its removal from the wall 193.

Needle assembly 26 is now prepared for introducing the augmenting solution into wall 193. In this regard, saline stop cock 298 is closed and DMSO stop cock 297 is opened to permit needle 61 to be primed with DMSO from syringe 287. In one preferred procedure, DMSO is supplied to needle 61 until approximately 0.3 cubic centimeters of the DMSO is viewed spraying freely into the esophagus 186 from openings 71 in needle distal end portion 61b. DMSO is then withdrawn from needle 61 leaving only a column of approximately three centimeters in the proximal end portion 61a of the needle 61. Such DMSO column in combination with the amount of DMSO within fluid connector 81 approximates 0.2 cubic centimeters. DMSO stop cock 297 is closed and stop cock 296 is opened to permit needle 61 to be slowly primed with approximately one cubic centimeter of the augmenting solution. During such priming step, the retained column of DMSO within needle assembly 26 is moved down needle 61 to distal end portion 61b so as to provide a leading column of DMSO approximating six centimeters. The remainder of needle assembly 26 is filled with a dense column of the augmenting solution.

In one procedure for creating an implant of the type described above having a volume of approximately one cubic centimeter, the following additional steps are performed. The physician closes the augmenting solution stop cock 296 and thereafter reopens DMSO stop cock 297. Needle distal end portion 61b is reinjected through the mucosa into saline pocket 227. In a preferred procedure, needle 61 reenters the puncture site used to create the pocket 227. The physician slowly pushes the plunger of DMSO syringe 287 to deliver approximately one cubic centimeter of DMSO to needle assembly and cause the leading column of DMSO within needle distal end portion 61b and the augmenting solution upstream of such DMSO column to be delivered to the pocket 227. Thereafter, needle distal end portion 61b is removed from the wall 193 and the supply of DMSO to needle assembly 26 continued so that approximately 0.3 cubic centimeters of the DMSO is sprayed freely from opening 71 into the esophagus 186. Such spraying can be viewed through the optical viewing device 23. The physician closes DMSO stop cock 297 and opens vent stop cock 306 to withdraw into vent syringe 308 the DMSO in needle assembly 26.

The vented DMSO can be optionally tested for the presence of augmenting solution therein by injecting it into a suitable aqueous solution. Any augmenting solution in the vented DMSO will precipitate in the aqueous solution. As a further assurance that needle assembly 26 is free of the augmenting solution, the physician can optionally open DMSO stop cock 297 and inject a sufficient quantity of DMSO into needle assembly 26 so that approximately 0.3 cubic centimeters of the DMSO sprays freely in a stream from needle distal end portion 61*b* into the esophagus 186.

In preparation for the next implantation, the physician tests needle assembly 26 to make certain that needle 61 deploys and retracts without difficulty. The physician next supplies a sufficient quantity of DMSO to the needle assembly so that about 0.3 cubic centimeters sprays freely from needle opening 71 into the esophagus 186. DMSO stop cock 297 is then closed and the saline solution stop cock 298 opened. Saline solution is delivered to needle assembly 26 until approximately one cubic centimeter is viewed spraying in a stream from needle opening 71 into the esophagus. The objective lens 37 of optical viewing device 23 is thereafter rinsed and the mucosal surfaces washed by a saline or other aqueous solution dispensed in a conventional manner from the distal end of probe 22.

Syringes 286-288 are checked to ensure that they are sufficiently full for the next injection. If refilling is necessary, luer fitting portion 313 can be used to refill the saline solution syringe 288. Similarly, vent syringe 308 can be removed and luer fitting portion 311 used to alternately refill augmenting solution syringe 286 and DMSO syringe 287. Luer fitting portions 313 and 311 permit these refill steps to be performed without disassembly of the supply assembly 276. Luer fitting portions 313 and 311 can also be used to clear any air bubbles from the supply assembly 276 and the needle assembly 26. Distal extremity 31*b* of the insertion tube 31 is redirected within esophagus 186 to start the next implantation by puncturing the mucosa in the manner described above.

In an alternate procedure for creating implants which are greater than approximately one cubic centimeter, the saline pocket is repunctured in the same manner as discussed above. Thereafter, augmenting solution from syringe 286 is supplied to the needle assembly 26 to inject the six centimeter leading column of DMSO and downstream augmenting solution within needle 61 into the pocket 227. The physician closes the augmenting solution stop cock 296 and opens the DMSO stop cock 297 and completes the formation of the implant by pushing the balance of the augmenting solution within needle 61 into the pocket using a column of approximately one cubic centimeter of DMSO. The physician thereafter proceeds in this implantation procedure in the same manner as discussed above with respect to the creation of implants of approximately one cubic centimeter.

The augmenting solution described above can be used in other gastrointestinal procedures for other than the treatment of gastroesophageal reflux disease and be within the scope of the present invention. For example, the solution herein can be used to augment luminal walls in the vicinity of fistulas to aid in the stenting or other treatment of fistulas. In addition, the solution can be used to bulk other muscles in a body such as muscles in the vicinity of the anal sphincter to treat incompetent anal sphincters. The solution also has applications for the treatment of veins and arteries. In this regard, the solution can be injected into veins in the lower esophagus to treat esophageal varices and into veins in the vicinity of ulcers to treat for example gastric ulcers. Similarly, the solution can be used for the treatment of hemorrhoids.

Delivery apparatus other than treatment device 21 can be used in performing the method of the present invention. In addition, although the method and apparatus of the invention have been described when utilizing a biocompatible polymer and a biocompatible solvent, the method and apparatus can be modified as necessary when other solutions such as those containing prepolymers are utilized. In an alternate embodiment, not shown, the method of the present invention can be performed without optional balloon assembly 211. The syringes or other reservoirs described herein can be manually operated, as shown, or automated. For example, a conventional single-speed, multi-speed, programmable or other syringe pump can be used for automation. In procedures where no saline or similar solution is utilized, the saline solution syringe and the related saline solution fluid flow hardware need not be provided in the treatment device. Furthermore, the method of the invention is not limited to the transesophageal or intraesophageal method described above. The augmenting method herein can also be performed by surgical procedures such as a laparotomy, thoracotomy, laparoscopy or thoracoscopy.

Figure 18:
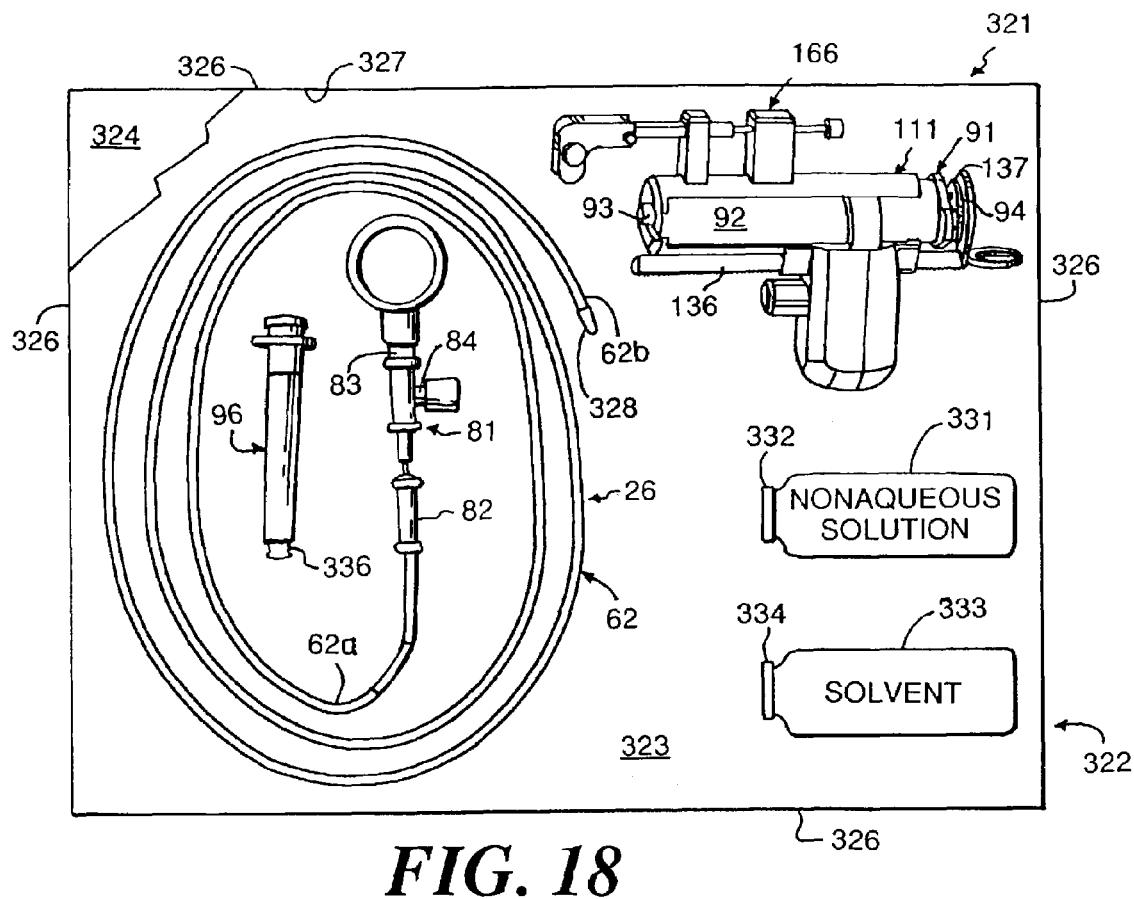
FIG. 18 is a plan view of a kit, somewhat schematic and partially cut away, for treating the upper portion of the gastrointestinal tract in accordance with the method of the present invention.

A kit 321 for a use in treating a wall forming the upper portion of a gastrointestinal tract in a human body in accordance with the method of the present invention is shown schematically in FIG. 18. Kit 321 includes a package 322 made from any suitable material such as cardboard or plastic for carrying the contents thereof. An exemplary package 322, shown in FIG. 18, is a box formed from a bottom wall 323, four side walls 324 and a top wall 326. A portion of top wall 326 is cut away in FIG. 18 to reveal an internal space 327 formed by walls 323, 324 and 326. The contents of receptacle or package 322 are disposed in internal space 327.

Needle assembly 26 is carried by package 322 within internal space 327. As discussed above, needle assembly 26 includes needle 61, sleeve 62 and fluid connector 81. A cap 328 is removably attached to distal end portion 62*b* of the sleeve 62 for protecting users against undesirable punctures by needle distal end portion 61*b* during storage and setup. Luer fitting portions 83 and 84 of fluid connector 81 are shown as being capped in FIG. 18. Kit 321 further includes reservoir or syringe 91 and a container or vial 331 of the nonaqueous or augmenting solution referred to above. Vial 331 has a cap 332 and luer fitting portion 93 of syringe 91 is removably couplable to cap 332. As discussed above, luer fitting portion 93 of the syringe 91 is also removably couplable to fluid connector 81 of needle assembly 26.

A delivery mechanism such as gun 111 for supplying a plurality of discrete preselected amounts of the nonaqueous solution from syringe 91 can optionally be included within kit 321. Syringe 91 is shown in FIG. 18 as being mounted within gun 111. Additional optional components of kit 321 include a second reservoir, such as syringe 96, and a container of a biocompatible solvent such as DMSO in the form of vial 333. Vial 333 includes a cap 334 and syringe 96 has a luer fitting portion 336 removably couplable to cap 334 of the vial 333. Kit 321 can optionally further include a plurality of stop cocks, such as stop cocks 101-103 and not shown in FIG. 18, for forming a manifold assembly 98 suitable for selectively directing the flow of liquid through needle assembly 26 in the manner discussed above. A third reservoir or syringe (not shown) and/or a vial of aqueous solution such as saline solution (not shown) can also be optionally included in kit 321.

Kit 321 can be used in any of the procedures described above or in any other procedure for treating wall 193 in the upper gastrointestinal tract. Needle assembly 26 of the kit 321 is preferably used with an elongate probe member such as probe 22 described above. In this regard, needle assembly 26 is diametrically sized for introduction into the gastrointestinal tract through probe 22 and, more particularly, through working channel 51 of probe insertion tube 31. Syringe 91 is loaded with the nonaqueous solution from vial 331 by any suitable means such as coupling luer fitting portion 93 of the syringe 91 to cap 332 of the vial 330. When filled, syringe 91 is attached to fluid connector 81 in a manner discussed above. Probe 22 is introduced into esophagus 186 until distal extremity 31b of insertion tube 31 is in the vicinity of the treatment area. Thereafter, distal end portions 61b and 62b of needle assembly 22 are advanced through insertion tube 31 until such distal end portions of needle 61 and sleeve 62 are in the vicinity of insertion tube distal extremity 31b.

Gun 111 or another suitable delivery mechanism can optionally be utilized in the procedure. When gun 111 is so used, syringe 91 is mounted within the gun in a manner discussed above. In addition, optional syringe 96 can be used for supplying a suitable biocompatible solvent such as DMSO through needle assembly 26 during the procedure. The syringe 96 is filled by removably coupling luer fitting portion 336 thereof to cap 334 of vial 333. Thereafter, the syringe 96 is coupled to fluid connector 81 in a manner discussed above. In addition, optional saline solution syringe 97 can be coupled to fluid connector 81 in a manner discussed above for use during the procedure.

As discussed more fully above in the procedure for treating gastroesophageal reflux disease, the nonaqueous solution from syringe 91 can be introduced into wall 193 in the vicinity of the lower esophageal sphincter 187 for bulking or otherwise treating the wall 193. In one such exemplary procedure discussed above, the nonaqueous solution is introduced into one or both of muscle layers 201 and 202 of wall 193 to form one or more nonbiodegradable implants, such as implants 236, in one or both of the muscle layers 201 and 202. Such implants can be formed above and/or below squamous columnar junction 198 and be formed in addition to or without other implants in esophageal mucosa 196 for submucosal space 203. A biocompatible solvent such as DMSO and/or an aqueous solution such as saline be optionally be utilized in the manner discussed above in such procedure.

Figure 19:
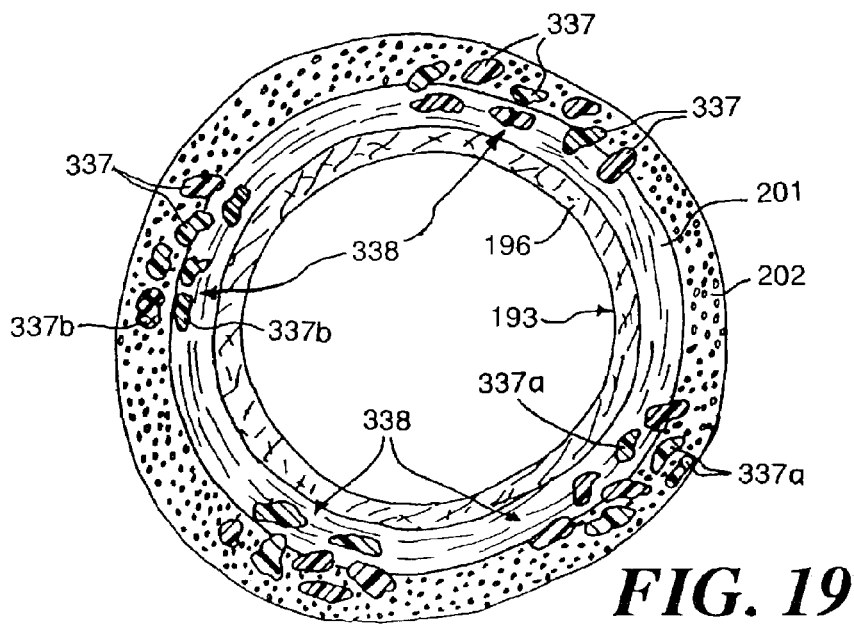
FIG. 19 is a cross-sectional view, similar to FIG. 9, of the lower esophageal sphincter at the level of the gastric cardia as treated by the method of the present invention.

Implants from an exemplary procedure in which a plurality of implants are formed in each of muscle layers 201 and 202 of the gastric cardia, that is below squamous columnar junction 198, are shown in FIG. 19. In such procedure, needle distal end portion 61b is introduced into one or both of muscle layers 201 and 202 of wall 193 in the manner discussed above. Thereafter, the nonaqueous solution within syringe 91 is delivered through needle assembly 26 into wall 193 in a pulsed manner, by means of gun 111 or any other manual or automated syringe or device, so as to create a plurality of small spaced-apart implants 337 in circular muscle layer 201 and/or longitudinal muscle layer 202. The volume of each pulse of nonaqueous solution can range from 0.25 to 5.0 cubic centimeters and more preferably from 0.5 to 2.0 cubic centimeters. One preferred speed of injection of the nonaqueous solution ranges from 0.50 to 2.0 cubic centimeters per minute. The pulsed introduction of the nonaqueous solution into wall 193 causes the solution to migrate from the opening in the needle distal end portion 61b so as to form a plurality of lake-like interdigitated implants 337.

Implants 337 are interspersed between muscle fibers and have an exemplary size ranging from 0.05 to 0.2 cubic centimeters and more preferably from 0.075 to 0.125 cubic centimeters. A plurality of implants 337 and, as shown in FIG. 19, a plurality of three implants 337a can be spaced apart across the thickness of wall 193. Similarly, a plurality of implants 337 and, as shown in FIG. 19, a plurality of two implants 337b can be spaced apart across the thickness of one or both of muscle layers 201 and 202. The implants 337 can be spaced apart completely around muscle layers 201 and 202, be grouped in circumferentially spaced-apart sets 338 of implants 337 around the layers 201 and 202 or be asymmetrically spaced around the layers 201 and 202. In the results shown in FIG. 19, four sets 338 of implants 337 are shown, each set 338 being spaced apart approximately 90° from adjacent sets 338. Such a plurality of closely spaced-apart implants 337 serve to reduce the distensibility of wall 193 and thereby modify the lower esophageal sphincter 187 to reestablish the reflux barrier. The stiffened sphincter is less likely to relax and permit reflux of food and/or other materials within stomach 188. Such closely spaced-apart implants 337 can be formed other than by pulsing the introduction of the nonaqueous solution, such as by continuous injection of the nonaqueous solution, and be within the scope of the present invention.

Other exemplary sizes and configurations of implants for use in the gastrointestinal tract are illustrated in FIG. 20, which shows a cross-sectional view of the gastric cardia similar to FIG. 19 that has been segmented to depict such other implants. As shown in one segment of wall 193 in FIG. 20, one or more implants 341 each having a size smaller than implants 337 can be formed in the wall 193 for reducing the distensibility of the wall. Such one or more implants 341 can be formed in one or both of muscle layers 201 and 202. A plurality of implants 341 can be spaced apart across the thickness of one or both of muscle layers 201 and 202. One or more implants 342 each having a size larger than implants 337 but smaller than implant 228 shown in FIGS. 7-9 can also be formed in one or both of muscle layers 201 and 202. Another segmented portion of wall 193 shown in FIG. 20 illustrates a plurality of two implants 342 formed in layers 201 and 202. One or more implants 343 which are other than round can also be formed in one or both of muscle layers 201 and 202 of wall 343, as shown in a further segmented portion of the gastric cardia depicted in FIG. 20. A plurality of two elongate thin implants 343, in combination with one implant 342, is shown in FIG. 20. Each of the elongate implants 343 can be formed from a single pulsed or continuous injection of a suitable material, such as the nonaqueous solution discussed above, or from the merger of two smaller implants formed in the wall 193. A plurality of implants 343 can be formed in one or both of muscle layers 201 and 202. A plurality of a single type of implant 337, 341, 342 or 343 or a combination of one or more implants 337 and 341-343 can be symmetrically or asymmetrically disposed around esophagus 186. Implants so formed in one or both of muscle layers 201 and 202 may or may not deform the surface forming esophagus 186 and thus may or may not partially or completely coapt the esophagus.

Each of the implants shown in FIG. 20 can be formed from a single or pulsed injection of any suitable material such as any of the materials discussed above. Other suitable materials for introduction into one or both of muscle layers 201 and 202 include injectable bioglass as described in Walker et al., "Injectable Bioglass as a Potential Substitute for Injectable Polytetrafluoroethylene Particles", J. Urol., 148:645-7, 1992, small particle species such as polytetrafluoroethylene (PTFE) particles in glycerine such as Polytef®, biocompatible compositions comprising discrete, polymeric and silicone rubber bodies such as described in U.S. Pat. Nos. 5,007,940, 5,158,573 and 5,116,387 to Berg, biocompatible compositions comprising carbon coated beads such as disclosed in U.S. Pat. No. 5,451,406 to Lawin, collagen and other biodegradable material of the type disclosed in U.S. Pat. No. 4,803,075 to Wallace et al. and other known injectable materials.

Kit 321 can be used for treating tracheo-esophageal fistulas in the manner described in copending application Ser. No. 09/286,531 filed Apr. 5, 1999, now U.S. Pat. No. 6,248,058. In such a procedure, a nonaqueous solution is introduced by needle 61 into wall 193 in the vicinity of the fistula to augment the wall and thus facilitate the retention of a stent placed in the esophagus to isolate the fistula. Kit 321 can also be used in further procedures within the upper gastrointestinal tract, such as the procedures described above for treating veins and arteries and for treating gastric ulcers. Needle 61 and sleeve 62 of needle assembly 26 are appropriately sized for the desired procedure. Specifically, each of needle 61 and sleeve 62 must have a length at least sufficient to permit distal end portions 61b and 62b to be in the vicinity of the treatment site when proximal end portions 61a and 62a are outside of the body. Probe 22 is appropriately sized in a similar manner.

In another method of the invention for treating the gastrointestinal tract, material can be introduced into the wall forming the lower gastrointestinal tract in the vicinity of the anus of a body to treat the anal sphincter. As shown in FIGS. 21-23, the gastrointestinal tract includes the rectum 346 and opens to the outside of body 184 at the anus 347. The inner layer of the wall 348 forming rectum 346 is mucosal layer 351. A layer of muscle extends around the rectum 346 and also forms part of rectal wall 348. Such muscle layer comprises circular muscle layer 352 extending beneath mucosal layer 351 and longitudinal muscle layer 353 extending beneath muscle layer 352. Body 184 further includes the anal sphincter 356 having the sphincter ani internus 357 and the sphincter ani externus 358. The sphincter ani internus 357 forms the terminus of circular muscle layer 352 at anus 347. The sphincter ani externus 358 comprises a deep external sphincter 361, the superficial external sphincter 362 and the subcutaneous external sphincter 363. For purposes of this application, rectal wall 348 and thus the wall of the gastrointestinal tract of body 184 includes both the sphincter ani internus 357 and the sphincter ani externus 358.

In the method for treating fecal incontinence of the present invention, a solution is introduced into rectal wall 348 in the vicinity of anal sphincter 356 by any suitable means to augment, bulk or otherwise decrease the distensibility of the anal sphincter 356. One preferred apparatus for introducing the solution into rectal wall 348 is a conventional syringe 366 having a barrel 367 filled with the solution. A conventional elongate needle 368 is connected to syringe 366 for delivering the solution from barrel 367 into rectal wall 348. Tubular needle 368 can be of a conventional type and, as such, provided with a single opening at the distal end thereof. Alternatively, needle 368 can be similar to any of the needles described above.

Any suitable material or solution, including without limitation any or the materials or solutions discussed above, can be utilized for augmenting, modifying the distensibility or otherwise treating rectal wall 348 in the vicinity of anus 347. In a preferred method of the invention, at least one nonaqueous solution is introduced into rectal wall 348 for forming a nonbiodegradable solid or implant in the rectal wall. In a particularly preferred method, the at least one solution is a solution of a biocompatible polymer and a biocompatible solvent. Once such solution is introduced into rectal wall 348, the biocompatible polymer precipitates from the solution so as to form an implant and the bio-compatible solvent disperses in body 184.

Any number and configuration of implants 371 can be formed in rectal wall 348. In one preferred method, a plurality of circumferentially spaced-apart implants 371 are formed in the rectal wall 348 (see FIGS. 21-22). The discrete implants 371 can be formed in mucosal layer 351, circular muscle layer 352 and/or longitudinal muscle layer 353. In addition, the implants 371 can be formed in anal sphincter 356, as shown in FIGS. 21-22 where the implants 371 are located in sphincter ani internus 357. It should be appreciated that implants 371 can also be formed in any or all of the portions of sphincter ani externus 358, namely, deep external sphincter 361, superficial external sphincter 362 and/or subcutaneous external sphincter 363. An exemplary implant 372 formed by dashed lines is shown in each of deep external sphincter 361, superficial external sphincter 362 and subcutaneous external sphincter 363 in FIG. 21.

When a plurality of implants 371 are formed in rectal wall 348 in the vicinity of anus 347, such implants can be disposed substantially in a plane, as shown in FIGS. 21-22, in multiple planes or out of plane. Implants 371 can be symmetrically or asymmetrically disposed around the anus 347. Implants similar to any of implants 337 and 341-343 can be formed in any portion of the wall 348, including portions of sphincter ani internus 357 or sphincter ani externus 358. Such implants can be formed from pulsed or continuous injections of a solution from syringe 366 or by any other suitable manual or automated means. The amount of any such solution injected into rectal wall 348 can range from 0.05 to 10 cubic centimeters and the rate of injection of the solution can range from 0.1 to 10 cubic centimeters per minute.

Other apparatus can be utilized for bulking rectal wall 348 in the vicinity of anus 347. For example, as shown in FIG. 23 a delivery mechanism or gun 376 which provides preselected amounts of the solution into rectal wall 348 can be utilized. Gun 376 is substantially similar to gun 111 and like reference numerals have been used to describe like components of guns 111 and 376. Gun 376 does not include the adjustment mechanism 166 of gun 111. Syringe 366 can be utilized with gun 376 and a stop cock 377 can be disposed between syringe 366 and needle 368 for permitting a biocompatible solvent such as DMSO and/or an aqueous solution such as saline to be alternatively introduced through needle 368 into rectal wall 348. Reservoirs such as respective syringes 96 and 97 can be utilized in this regard.

It can be seen from the foregoing that the implants formed by the method of the present invention can be of a variety of sizes and formed in a variety of configurations in the wall of the gastrointestinal tract. Any material or solution utilized for forming such implants can be injected into the wall in a variety of manual or automated and pulsed on continuous manners. One or more implants can be formed in any of the layers of the wall, including any of the muscle layers of the wall. Without limiting the foregoing, it should be appreciated that any of the implants of the invention, such as implants 337 and 341-343, can be formed in any sphincter-like muscle or mechanism in the gastrointestinal tract or elsewhere in the body.

From the foregoing, it can be seen that a minimally invasive method and apparatus for treating gastroesophageal reflux disease has been provided. A nonbiodegradable material is injected in the wall forming the esophagus and/or stomach in the vicinity of the lower esophageal sphincter for bulking such wall. The material is injected as at least one solution and thereafter forms a solid. In one embodiment, the at least one solution includes a solution from which a nonbiodegradable solid precipitates. In a more specific embodiment, the solution includes a biocompatible polymer and a biocompatible solvent. An aqueous or physiologic solution can optionally be introduced into the wall to condition the wall.

What is claimed is:

1. A kit for use in treating a wall forming the upper portion of a gastrointestinal tract in a body of a human having an esophagus extending from a mouth through a lower esophageal sphincter to a stomach comprising a package, a needle assembly carried within the package and consisting of a single-walled flexible elongate tubular member having proximal and distal extremities and a tubular needle slidably disposed in the flexible elongate tubular member and movable from a retracted position in which the tubular needle is recessed within the distal extremity of the flexible elongate tubular member to an extended position in which the tubular needle projects distally of the flexible elongate tubular member, the flexible elongate tubular member having a length of at least approximately 34 centimeters so that when the distal extremity is in the vicinity of the lower esophageal sphincter the proximal extremity is outside of the body, and a fluid connector carried by the proximal extremity of the flexible elongate tubular member and coupled to the tubular needle, a syringe removably couplable to the fluid connector carried within the package and a container of a solution of a biocompatible polymer and a biocompatible solvent for forming a nonbiodegradable solid carried within the package whereby the solution is loaded from the container into the syringe and delivered from the syringe by means of the needle assembly into the wall to form a nonbiodegradable solid in the wall.

2. The kit of claim 1 wherein the flexible elongate tubular member is made from flexible plastic.

3. The kit of claim 1 further comprising an additional syringe and a container of the biocompatible solvent carried within the package.

4. The kit of claim 1 further comprising a delivery mechanism for supplying a plurality of discrete preselected amounts of the solution from the syringe to the needle assembly for introduction into the wall.

5. The kit of claim 1 wherein the solution includes a contrast agent for facilitating visualization of the nonbiodegradable solid in the wall.

6. A kit for use in treating a wall forming the upper portion of a gastrointestinal tract in a body of a human having an esophagus extending from a mouth through a lower esophageal sphincter to a stomach comprising a package, a needle assembly carried within the package and consisting of a single-walled flexible elongate tubular member having proximal and distal extremities and a tubular needle slidably disposed in the flexible elongate tubular member and movable from a retracted position in which the tubular needle is recessed within the distal extremity of the flexible elongate tubular member to an extended position in which the tubular needle projects distally of the elongate tubular member, the flexible elongate tubular member having a length of at least approximately 34 centimeters so that when the distal extremity is in the vicinity of the lower esophageal sphincter the proximal extremity is outside of the body, and a fluid connector carried by the proximal extremity of the flexible elongate tubular member and coupled to the tubular needle, and a container of a solution of a biocompatible polymer and a biocompatible solvent for forming a nonbiodegradable solid carried within the package whereby the solution in the container is delivered by means of the needle assembly into the wall to form a nonbiodegradable solid in the wall.

7. The kit of claim 6 wherein the flexible elongate tubular member is made from flexible plastic.

8. A kit for use in treating a wall having tissue and forming the upper portion of a gastrointestinal tract in a body of a human having an esophagus extending from a mouth through a lower esophageal sphincter to a stomach comprising a package, a needle assembly carried within the package and consisting of a single-walled flexible elongate tubular member having proximal and distal extremities and a tubular needle slidably disposed in the flexible elongate tubular member and movable from a retracted position in which the tubular needle is recessed within the distal extremity of the flexible elongate tubular member to an extended position in which the tubular needle projects distally of the flexible elongate tubular member, the flexible elongate tubular member having a length of at least approximately 34 centimeters so that when the distal extremity is in the vicinity of the lower esophageal sphincter the proximal extremity is outside of the body, and a connector carried by the proximal extremity of the flexible elongate tubular member and coupled to the tubular needle, a syringe removably couplable to the connector carried within the package and a container of a prepolymer composition for forming a nonbiodegradable solid carried within the package whereby the prepolymer composition is loaded from the container into the syringe and delivered from the syringe by means of the needle assembly into the tissue of the wall to form a nonbiodegradable solid in the tissue of the wall.

9. The kit of claim 8 wherein the flexible elongate tubular member is made from flexible plastic.

10. The kit of claim 8 wherein the container further includes a contrast agent for facilitating visualization in the wall of the body.

11. The kit of claim 8 further comprising a container of a biocompatible solvent carried within the package.

* * * * *